United States Patent
Coelho et al.

(10) Patent No.: US 8,167,139 B2
(45) Date of Patent: *May 1, 2012

(54) STEM AND PROGENITOR CELL COMPOSITIONS RECOVERED FROM BONE MARROW OR CORD BLOOD; SYSTEM AND METHOD FOR PREPARATION THEREOF

(75) Inventors: Philip H. Coelho, Sacramento, CA (US); Bruce A. Baker, Placerville, CA (US); John R. Chapman, Sacramento, CA (US); Junzhi Li, Gold River, CA (US); Prince Emmanuel, Sacramento, CA (US); Robert S. Childers, Lincoln, CA (US)

(73) Assignee: ThermoGenesis Corp., Rancho Cordova, CA (US)

(*) Notice: Subject to any disclaimer, the term of this patent is extended or adjusted under 35 U.S.C. 154(b) by 513 days.

This patent is subject to a terminal disclaimer.

(21) Appl. No.: 11/825,542

(22) Filed: Jul. 6, 2007

(65) Prior Publication Data
US 2007/0269887 A1    Nov. 22, 2007

Related U.S. Application Data

(63) Continuation-in-part of application No. 10/118,291, filed on Apr. 8, 2002, now Pat. No. 7,241,281, and a continuation-in-part of application No. 11/664,212, filed as application No. PCT/US2005/029288 on Aug. 16, 2005.

(51) Int. Cl.
*B01D 24/32* (2006.01)
*B04B 5/02* (2006.01)
*A61M 37/00* (2006.01)
*B04B 5/00* (2006.01)

(52) U.S. Cl. ............ 210/361; 210/782; 210/86; 210/91; 210/103; 210/362; 494/16; 494/20; 494/21; 494/37; 604/6.15; 604/403; 604/408; 604/410; 604/500

(58) Field of Classification Search .................. None
See application file for complete search history.

(56) References Cited

U.S. PATENT DOCUMENTS 2,402,496 A  *  6/1946  Hertrich ..................... 415/43
3,987,961 A     10/1976  Sinn et al.
(Continued)

FOREIGN PATENT DOCUMENTS
WO    WO 95/01842 A1    1/1995

*Primary Examiner* — Krishnan S Menon
(74) *Attorney, Agent, or Firm* — Weintraub Genshlea et al.; Audrey A. Millemann; Dennis A. DeBoo

(57) ABSTRACT

The invention includes compositions of stem and progenitor cells recovered from bone marrow or cord blood containing most of the viable CD34+ cells and substantially depleted of red blood cells resident in the original sample, without any xenobiotic additives to aid cell separation. The invention also includes a system and method for preparing the compositions. The system includes a bag set and a processing device, which utilizes an optical sensor, microcontroller, servo motor, accelerometer, load cell, and battery. The system and method utilize centrifugation to stratify the cells into layers and then separate and transfer the stem cells into a stem cell bag. The processing device's microcontroller receives input from the device's accelerometer, load cell and optical sensor to direct the metering valve in the bag set to open and close to permit the transfer of as many stems cells as possible with as few red cells as possible.

5 Claims, 20 Drawing Sheets

U.S. PATENT DOCUMENTS

| | | | |
|---|---|---|---|
| 4,120,448 A | 10/1978 | Cullis | |
| 4,447,220 A | 5/1984 | Eberle | |
| 4,608,178 A | 8/1986 | Johansson et al. | |
| 4,720,284 A | 1/1988 | McCarty | |
| 4,946,434 A | 8/1990 | Plaisted et al. | |
| D314,824 S | 2/1991 | Moon | |
| 5,102,407 A | 4/1992 | Carmen et al. | |
| 5,330,562 A | 7/1994 | Anderson | |
| 5,484,428 A | 1/1996 | Drainville et al. | |
| 5,674,173 A | 10/1997 | Hlavinka et al. | |
| 5,723,050 A | 3/1998 | Unger et al. | |
| 5,769,839 A | 6/1998 | Carmen et al. | |
| 5,792,038 A | 8/1998 | Hlavinka et al. | |
| 5,836,934 A | 11/1998 | Beshel | |
| 5,921,950 A | 7/1999 | Toavs et al. | |
| 6,251,284 B1 | 6/2001 | Bischof et al. | |
| 6,315,706 B1 | 11/2001 | Unger et al. | |
| 6,322,709 B1 | 11/2001 | Krasnoff et al. | |
| 6,348,031 B1 | 2/2002 | Unger et al. | |
| 6,471,855 B1 | 10/2002 | Odak et al. | |
| 6,495,039 B1 | 12/2002 | Lee et al. | |
| 6,652,475 B1 | 11/2003 | Sahines et al. | |
| 7,179,391 B2 | 2/2007 | Leach et al. | |
| 2002/0082153 A1 * | 6/2002 | Jorgensen et al. | 494/2 |

* cited by examiner

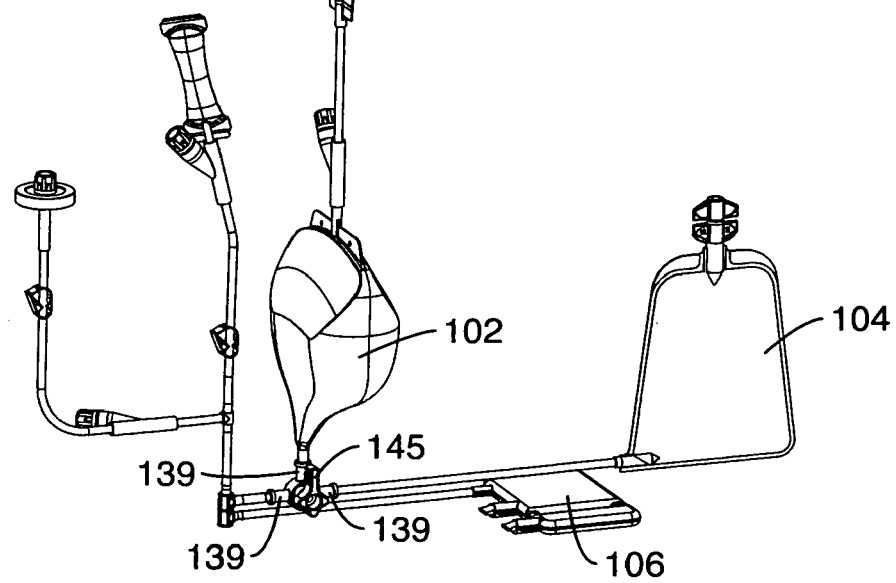
FIG. 2

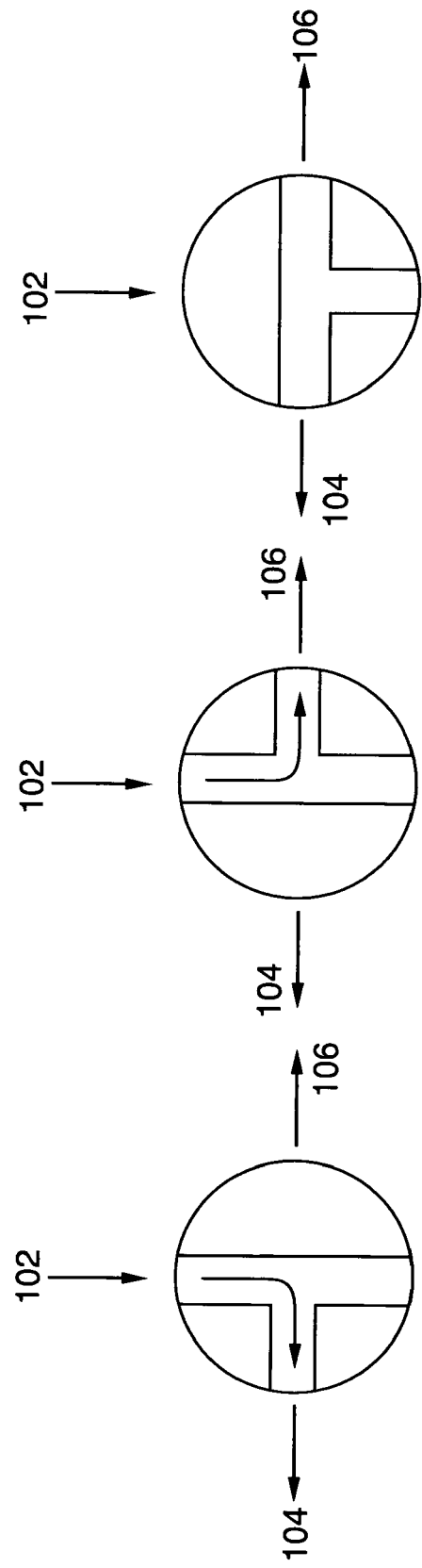

STEM AND PROGENITOR CELL COMPOSITIONS RECOVERED FROM BONE MARROW OR CORD BLOOD; SYSTEM AND METHOD FOR PREPARATION THEREOF

CROSS-REFERENCE TO RELATED APPLICATIONS

Pursuant to 35 U.S.C. §120, this application is a continuation-in-part of and claims priority to U.S. patent application Ser. No. 10/118,291 filed on Apr. 8, 2002, now U.S. Pat. No. 7,241,281, the entire disclosure of which is incorporated herein by reference.

Pursuant to 35 U.S.C. §120, this application is also a continuation-in-part of and claims priority to co-pending U.S. patent application Ser. No. 11/664,212 filed on Mar. 28, 2007, which is a 35 U.S.C. §371 national phase application from and claims priority to international application serial no. PCT/US2005/029288 filed on Aug. 16, 2005 which designated the United States and which was published in English under PCT Article 21(2) on Apr. 13, 2006 as International Publication No. WO 2006/038993 A2, and which in turn claimed priority to U.S. patent application Ser. No. 10/957,095 filed on Sep. 30, 2004 which issued as U.S. Pat. No. 7,211,191 on May 1, 2007, all disclosures of which are incorporated herein by reference in their entirety.

BACKGROUND OF THE INVENTION

1. Field of the Invention

The invention relates generally to methods and apparatus for recovering specific cell populations from human bone marrow or cord blood. In particular, the invention includes a system and method for the high efficiency recovery (isolating and separating) of stem and progenitor cells, resident in bone marrow or cord blood, and the removal of excess red cells, neutrophils, platelets, and plasma, without the aid of xenobiotic additives typically employed to improve the efficiency of stem cell recovery. The system includes a sterile, functionally closed bag set and a microprocessor controlled electrical mechanical and optical device designed to operate in a centrifugal field that separates the cell populations based on their size and density and then transfers these stem and progenitor cells in a predetermined final volume to a stem cell bag. The invention also includes compositions of stem and progenitor cells prepared from human bone marrow or cord blood which would be for immediate use or for storage and later use.

2. Description of the Related Art

For purposes of this specification and the claims, the following definitions are used:

"Autologous use" means the implantation, transplantation, infusion, or transfer of human cells or tissue back into the individual from whom the cells or tissue were recovered.

"Crystalloid" means an isotonic salt and/or glucose solution used for electrolyte replacement or to increase intravascular volume, such as saline solution, Ringer's lactate solution, or 5 percent dextrose in water.

"Hematopoietic stem cell" is a pluripotent stem cell that gives rise to the many types of blood cells including red blood cells (RBCs), leukocytes, white blood cells (WBCs), and platelets.

"Leukocytes" or white blood cells are cells in the hematopoietic lineage which include principally monocytes, lymphocytes, and neutrophils and express the cell surface antigen CD45 (CD45+ cells).

"Lymphocytes" are cells of the lymphoid lineage as measured by the Sysmex XE-2100 which can include mature lymphocytes (T cells, B cells, NK cells) and developing lymphocytes such as lymphoblasts.

"Minimally manipulated bone marrow or cord blood" means the processing of anticoagulated (such as with heparin or citrate) bone marrow or cord blood for stem and progenitor cells that does not include the addition of chemical substances (except for water, crystalloids, or a sterilizing, preserving, or storage agents), and does not alter the relevant biological characteristics of the cells or tissues.

"Monocytes" are cells of the myeloid lineage as measured by the Sysmex XE-2100 which can include mature monocytes and developing monocytes such as monoblasts.

"Mononuclear cells" (MNC) are cells in the hematopoietic lineage which include monocytes and lymphocytes.

"Neutrophils" are cells of myeloid lineage as measured by the Sysmex XE-2100 which can include polymorphonuclear neutrophils and developing neutrophils such as the band form, metamyelocyte, myelocyte, and myeloblast.

"Platelets" are cells of the megakaryocyte line as measured by the Sysmex XE-2100 which can include mature platelets (thrombocytes).

"Progenitor cells" are a direct progeny of the stem cell that give rise to a distinct cell lineage by a series of cell divisions.

"Red cells" Cells of the erythroid line as measured by the Sysmex XE-2100 which include mature RBC but not nucleated red cells.

"Stem cells" are pluripotent cells that have three general properties: (1) they are capable of dividing and renewing themselves for long periods; (2) they are unspecialized; and (3) they can give rise to different specialized cell types. A cell surface antigen marker for stem cells is the CD34 antigen as is the elevated concentration of the intracellular enzyme aldehyde dehydrogenase (ALDH).

"Stoke's Law" is a mathematical formula ($V_g = d^2(P1-P2)/18\mu \times G$) that describes the sedimentation velocity of a particle in a viscous liquid during gravitational acceleration, wherein:

$V_g$=sedimentation velocity,
d=particle diameter,
P1=particle density,
P2=liquid density,
G=gravitational acceleration, and
$\mu$=viscosity of liquid.

"Sysmex XE-2100" is an automated hematology cell analyzer manufactured by Sysmex Corp, Kobe, Japan that differentiates and quantitates hematopoietic cells by flow cytometry, emitting a semiconductor laser beam, and detecting three optical signals: forward scatter, side scatter, and side fluorescence.

"Total nucleated cells" (TNC) are WBCs and nucleated RBCs.

"Xenobiotic additive" and "xenobiotic agent" mean a chemical substance which is not a natural component of the human body that is intentionally added to the collected bone marrow or cord blood for the purpose of achieving a change in the cell separation process performance characteristics that would not occur if it was not added.

Examples of xenobiotic additives are:

1. sedimentation agents (e.g., hydroxy ethyl starch, dextran, or gelatins);
2. density gradient media (e.g., Ficoll®, Percoll®); and
3. affinity molecules for cell surface macromolecules cells (e.g., monoclonal antibodies, monoclonal antibodies bound to paramagnetic beads).

To date, despite the enormous clinical potential of stem cells, no stem cell therapies have received FDA clearance for human use. A major barrier to demonstrating clinical efficacy and safety and obtaining regulatory clearance of a stem cell therapy is that the existing devices and methods used to separate the stem cell populations from bone marrow or cord blood have one or more of the following significant limitations: they are open systems risking microbial contamination; they are time and labor intensive; they require the addition of undesirable and expensive xenobiotic agents; they recover stem cells at a very low efficiency, averaging 40 to 75%; and they are not compatible with the volume of cord blood or bone marrow utilized for tissue regeneration.

Before broad scale use of stem cells to treat serious and frequent human diseases, such as myocardial infarction, ischemia, diabetes and dermal wounds can occur, three critical hurdles must be overcome:

1. Clinical trials must demonstrate efficacy and safety of the stem cell therapy;

2. Regulatory clearance by government health agencies, in particular, the Food and Drug. Administration (FDA) Office of Cell, Tissue and Gene Therapy (OCTGT) in the United States, must be obtained; and 3. A practical method for the rapid and simple recovery of viable stem and progenitor cells from minimally manipulated bone marrow or cord blood that does not rely on the use of xenobiotic additives to remove excess plasma, red cells, and granulocytes must be developed.

In addition to hematopoietic stem cells, it is now known that bone marrow and cord blood contain other types of stem and progenitor cells of potential therapeutic value for tissue regeneration and to enhance wound healing. Mesenchymal stem cells previously designated as bone marrow stromal cells can give rise to bone, cartilage, fat, muscle, and connective tissue and are ALDH Br+. Endothelial progenitor cells, resident in the bone marrow, are primitive cells descended from hematopoietic stem cells, can enter the bloodstream and go to areas of blood vessel injury to help repair the damage, can give rise to new blood vessels, and are CD34+.

Stem cells are identified by various cell surface markers, including CD34+ and aldehyde dehydrogenase bright cells (ALDH Br+). CD34+ cells are stem cells that express an antigen designated as CD34 which can be detected by using a chromophore conjugated antibody with specificity to that particular antigen. Other researchers identify adult stem cells based upon their expressing high levels of the enzyme aldehyde dehydrogenase (ALDH). One company, Aldagen (Durham, N.C.) developed a technology which utilizes a substrate that detects cells expressing high levels of ALDH by generating an intense green fluorescence. These so-called ALDH bright cells (ALDH Br+) can be detected using flow cytometry. ALDH Br+ cells contain different progenitors that can give rise to a variety of important cell lines, including neurological and endothelial cells.

Viability of stem cells can be demonstrated by several methods including exclusion of a vital dye such as trypan blue or 7-amino-actinomycin D (7-AAD). Viability of stem cells is routinely assessed by measuring the viability of white blood cells (CD45+ cells) as a surrogate for the stem cells in the bone marrow or cord blood using commercially available kits.

Large volumes of bone marrow or cord blood are unwieldy, especially because of the presence of a large number of red cells (there are approximately 25,000 red cells for each CD34+ cell in bone marrow and approximately 180,000 red cells for each CD34+ cell in cord blood). These excess red cells make it difficult to use the stem and progenitor cells because their presence radically dilutes the concentration of stem and progenitor cells at a wound site requiring tissue regeneration and they interfere with other processing steps for stem cells, including cultivating for ex-vivo cell expansion, gene therapy, or affinity purification of cell populations. Further, the presence of such a large number of red cells raises other safety issues, such as ABO incompatibility in allogeneic transplantation. In some cases, it may also be desirable to minimize neutrophils from the volume reduced stem cell concentrate due to the potential association of these cells with inflammatory reactions and the presence of biologically active enzymes and cytokines in their cytoplasm that could affect the viability or plasticity or otherwise change the functionality of stem cells.

The rate of movement and final location of a cell after a fixed period of centrifugation is a function of its size and density with its movement being defined according to Stoke's Law. Stem cells are lower in density than RBCs and higher in density than platelets, having a density closer to that of WBCs. Thus, the conventional method of recovering stem cells by density and size typically involves stratifying the cell population by centrifugation and then, after removal from the centrifuge, attempting to capture the stem cells from the remainder of the cord blood or bone marrow.

One manual method of isolating WBCs and stem cells from bone marrow or cord blood is to insert whole bone marrow or cord blood into centrifuge tubes and spin them at 1500-2000×g for 10-15 min at room temperature. This separates the bone marrow or cord blood into an upper plasma layer, a lower red blood cell (RBC) layer, and a thin layer of WBCs and stem and progenitor cells at the interface between the RBC and plasma. After the stratification is accomplished, a disposable, plastic transfer pipette can be used to aspirate off the plasma (upper layer) down to about 1 mm from the RBCs. When removing the plasma, great care must be taken to not disturb the WBC/stem and progenitor cell layer which must be removed by the same pipetting technique while attempting to guard against loss of stem and progenitor cells into the RBCs or excessive contamination of the stem cells with RBCs. The disadvantages of this manual approach in test tubes are that it is an open system which risks microbial contamination of the bone marrow unit; it is labor and time intensive; the amount of red cell contamination of the WBC/stem and progenitor cell layer is highly variable; and the loss of stem cells is significant and variable. Microbial contamination, a major concern with this method, is important to avoid as it can negatively impact the ability to culture the stem cells or risk the transmission of infection to the body of the recipient of the stem cells.

Another method of recovering WBC/stem and progenitor cell populations from cord blood or bone marrow utlizes cell processing equipment such as the Compomat G4 device (Fresenius Kabi A G, Friedberg, Germany) and the COBE 2991 Blood Cell Processor (COBE Laboratories, Lakewood, Colo.). An example of this type of process is presented in Tsubaki, et al. "Concentration of Progenitor Cells Collected from Bone Marrow Fluid Using a Continuous Flow Cell Separator System", *Apheresis and Dialysis* 5 (1), 46-48, 2001. The amount of bone marrow or cord blood harvested for stem cells depends on the proposed clinical use. For cell based therapies in tissue regeneration or repair, typically 50-150 mL of bone marrow or cord blood is collected. These blood bank instruments require large volumes of bone marrow or cord blood (over 200 mL) to function properly and are entirely unsuited for the low volumes typically collected for tissue regeneration medical applications (less than 200 mL). In addition, the final volume of the cellular product (50-100 mL) of these mechanized processes is substantially larger than the preferred, final volume of 3-20 mL that provides the concentration of stem and progenitor cells appropriate for clinical use. These instruments also require pumps to move the blood or bone marrow from one container to another and these pumps can potentially cause mechanical damage to the cells.

Another method for volume reduction and purification of bone marrow or cord blood utilizes a gradient media such as Ficoll® or Percoll® to combine with the bone marrow or cord blood and, during centrifugation, interpose itself between the cell populations to reduce the mixing of cell populations during attempts to recover the stem cells. Ficoll® is a neutral, highly branched, high-mass, hydrophilic polysaccharide. Ficoll® (e.g. density of 1.077) can be used to separate blood or bone marrow into its components (erythrocytes, leukocytes, etc.). Ficoll® is normally placed at the bottom of a tube, and bone marrow or cord blood diluted with saline is then slowly layered above the Ficoll®. After being centrifuged, the heavier RBCs (density 1.09-1.10) displace the Ficoll® at the bottom of the tube and the following layers will be visible in the column, from top to bottom: (1) plasma and platelets; (2) mononuclear cells (MNC) (density 1.06-1.07); (3) Ficoll®; and (4) erythrocytes and neutrophils (density 1.08-1.09) present in pellet form at the bottom. This separation allows a harvest of MNCs with less chance of co-mingling the MNCs with the RBCs. Some red blood cell trapping (presence of erythrocytes and neutrophils) still occur in the MNC layer.

A significant disadvantage of processing bone marrow or cord blood with Ficoll® is that it is an open system at the step of adding the Ficoll® to the bone marrow or cord blood, meaning that microbes can enter directly into the bone marrow or cord blood and thereby increase the risk of microbial contamination. To reduce this risk, it is necessary to perform this step using a biological safety cabinet which may not always be available and is an expensive piece of laboratory equipment that must be continually maintained and monitored for acceptable performance. Further, Ficoll® is a xenobiotic and must be removed by washing before the cells can be safely administered to the human body. This washing step requires time and effort and further increases the potential for microbial contamination and loss of cells. The recovery of stem cells is low and highly variable, ranging from 20 to 70%. Percoll®, a colloidal silica coated with polyvinylpyrrolidone, is another density gradient media similar to Ficoll® with its attendant disadvantages.

A technique for isolation of bone marrow white blood cells using hydroxyethyl starch (HES) sedimentation agent has been published by A. Montuoro et al., "A technique for isolation of bone marrow cells using hydroxyethyl starch (HES) sedimentation agent," *Haematologica* 76 Suppl 1:7-9, 1991. HES is used clinically as a plasma expander and is characterized by its molecular weight and its degree of substitution. The addition of HES typically in a final concentration of 0.5 to 2% weight of HES to volume of bone marrow or cord blood causes the agglutination of red cells and thereby changes their sedimentation velocity based upon the principals of Stoke's Law. However, HES is a xenobiotic and has been associated with adverse events in some patients when administered intravenously. Further, the use of HES adds cost and additional complexity to cell processing. Dextran polymer preparations and gelatin solutions have also been used for the same purpose and have the same disadvantages as HES.

Finally, it is also known that stem and progenitor cells can be isolated from bone marrow or cord blood by the use of immunological methods, including flow cytometry cell sorting (Beckton Dickinson or Coulter) and by antibody coated paramagnetic particle cell sorting such as the Miltenyi Clini-Macs or Baxter Isolex systems. Antibodies with specificity to stem cell antigens, such as CD34, are employed as part of these separation technologies. These methods have the disadvantage of requiring expensive xenobiotic agents, equipment and disposable processing sets and are time consuming to perform. While the final product is a more pure population of stem cells with little red cell or leukocyte contamination, this level of purity represents a significant incurred expense and may not be required to achieve the intended cell therapy effect. Further, the addition of the antibodies and beads to the bone marrow or cord blood means the product was not "minimally manipulated" during the process as these reagents may cause unintended adverse biological consequences such as irreversible stem cell differentiation into lineage committed pathways.

A study by Minguell, et al. "Preparative separation of nucleated cells from human bone marrow", *Experentia* 35:548-549, 1978, compared volume reduction, cell recovery, and cell viability as a result of processing with dextran, dextran plus Ficoll®, Ficoll® and a buffy coat method. The paper demonstrates the lack of an ideal preparative process for bone marrow in that some of the processes caused loss of cell viability, and all had relatively low cell recovery of lymphoid cells (monocytes and lymphocytes or MNC) of 68% or less. To achieve the observed erythrocyte (RBC)/nucleated cell ratio of 2.7:1, the centrifugation method without sedimentation aid designated as the buffy coat method had a range of lymphoid cell recovery of these cells initially present that was low and highly variable, ranging from 36 to 68%.

SUMMARY OF THE INVENTION

There is a need for a system and method for preparing a composition of stem cells from bone marrow or cord blood that selectively recovers a high percentage of stem cells and a very low percentage of the RBCs; is quick, not labor intensive, and easy to perform in a consistent fashion; may be used in the operating room; is performed in a sterile, functionally closed system; requires no xenobiotic additives; reduces the original volume of the sample of bone marrow or cord blood; is capable of processing a range of volumes of bone marrow; and permits the user to select in advance the volume of the final product. There is also a need for a stem cell composition that includes a high percentage of the stem cells from the original sample and maintains those stem cells in a viable condition, contains a very low percentage of the RBCs from the original sample, does not include any xenobiotic additives, and has a final volume that can be selected by the user.

A composition of stem cells derived from human bone marrow or cord blood and a system and method for its preparation are disclosed. The disclosed invention has the following ten attributes integrated into a single system:
 1. it recovers a high percentage of stem cells;
 2. it reduces the original volume of the sample of bone marrow or cord blood by removal of excess plasma, RBCs, platelets, and neutrophils;
 3. it requires no xenobiotic additives to accomplish the stem cell recovery while enhancing the safety profile of the product, eliminating the need for cell washing, and minimizing cost;
 4. it maintains the stem cells in a viable condition;
 5. it is quick to complete (less than 90 minutes);
 6. it is not labor intensive due to automation of stem cell separation and capture steps;
 7. it is easy to perform in a consistent fashion requiring minimal operator training and expertise;
 8. it may be used in or adjacent to an operating room for autologous or allogenic use or in a cell processing laboratory;

9. it separates and isolates the stem and progenitor cells in a sterile, functionally closed system to reduce the risk of microbial contamination of a product; and 10. it is capable of processing the full range of bone marrow and cord blood used for tissue regeneration.

In one aspect, the invention includes a system which includes a processing bag set and a processing device. The bag set, which is sterile and preferably disposable, includes a processing bag, an RBC concentrate bag, a stem cell bag, a metering valve, and lines that connect the metering valve to each bag. Once the cord blood or bone marrow has been transferred into the processing bag, the bag set is placed into the processing device which fits into a centrifuge bucket. The processing device interacts with the bag set to transfer the WBC/stem and progenitor cell layer from the bone marrow or cord blood into the stem cell bag during a single centrifugation run. The processing device includes an optical sensor, a microcontroller, a servo motor, one or more accelerometers, a load cell, and a battery. The microcontroller receives and analyzes inputs from the optical sensor, accelerometers, and load cell, and directs the servo motor to open and close the metering valve, with precision valve movements, which allows the different cell layers stratified by density and size during the centrifugation to be transferred into different bags.

In another aspect, the invention also includes a method for separating and concentrating stem cells from bone marrow or cord blood. The method includes the following steps. The bone marrow or cord blood is transferred into the processing bag. The loaded bag set is placed into the processing device. The bag set is centrifuged in the processing device at a sufficient g force and time to stratify the cells of the bone marrow or cord blood in the processing bag into layers based on their density and size. The bag set is centrifuged in the processing device at a lower g force to allow separation and transfer of most of the RBCs from the processing bag into the RBC concentrate bag. The bag set may optionally be centrifuged in the processing device at a sufficient g force and time to restratify the cells in the processing bag into layers based on cell density and size. The bag set is centrifuged in the processing device while the metering valve rapidly opens and closes multiple times in succession to separate a portion of the remaining RBCs from the processing bag into the RBC concentrate bag without also transferring the WBC/stem and progenitor cell layer. While the bag set is being centrifuged, the processing device tares the weight of the empty stem cell bag to zero. The bag set is centrifuged in the processing device while the metering valve rapidly opens and closes multiple times in succession to separate and transfer the small amount of remaining RBCs, the WBC/stem and progenitor cell layer, and some plasma from the processing bag into the stem cell bag.

In another aspect, the invention includes stem and progenitor cell compositions derived from bone marrow or cord blood prepared by an embodiment of the method of the invention. The stem and progenitor cell composition from bone marrow has a ratio of about 1 CD34+ cell to about 500 RBCs, and, from cord blood, 1 CD34+ cell to 5,000 RBCs. These stem and progenitor cell compositions do not contain any xenobiotic additives.

The invented stem cell compositions address the current unmet clinical needs for stem and progenitor cell compositions prepared rapidly in a functionally closed bag set without the need for xenobiotic additives to achieve previously unattainable red cells to stem cell ratios. The bone marrow composition is advantageous in that it recovers a high proportion of CD34+ cells (about 97%) and ALDH Br+ cells (about 92%), while depleting about 98% of the RBCs, and contains no xenobiotic additives. The cord blood composition is also advantageous in that it recovers a high proportion CD34+ cells (about 95%), while depleting about 98% of the RBCs, and contains no xenobiotic additives.

BRIEF DESCRIPTION OF THE DRAWINGS

FIG. 2 is a perspective view of the bag set of FIG. 1.

FIG. 3A is a schematic diagram showing one fluid path of the metering valve of the bag set of FIG. 1.

FIG. 3B is a schematic diagram showing a second fluid path of the metering valve shown in FIG. 3A.

FIG. 3C is a schematic diagram showing a third fluid path of the metering valve shown in FIG. 3A.

DETAILED DESCRIPTION OF THE INVENTION

System for Recovering Stem and Progenitor Cell Compositions from Bone Marrow or Cord Blood The system includes bag set 100 and processing device 200.

Figure 1:
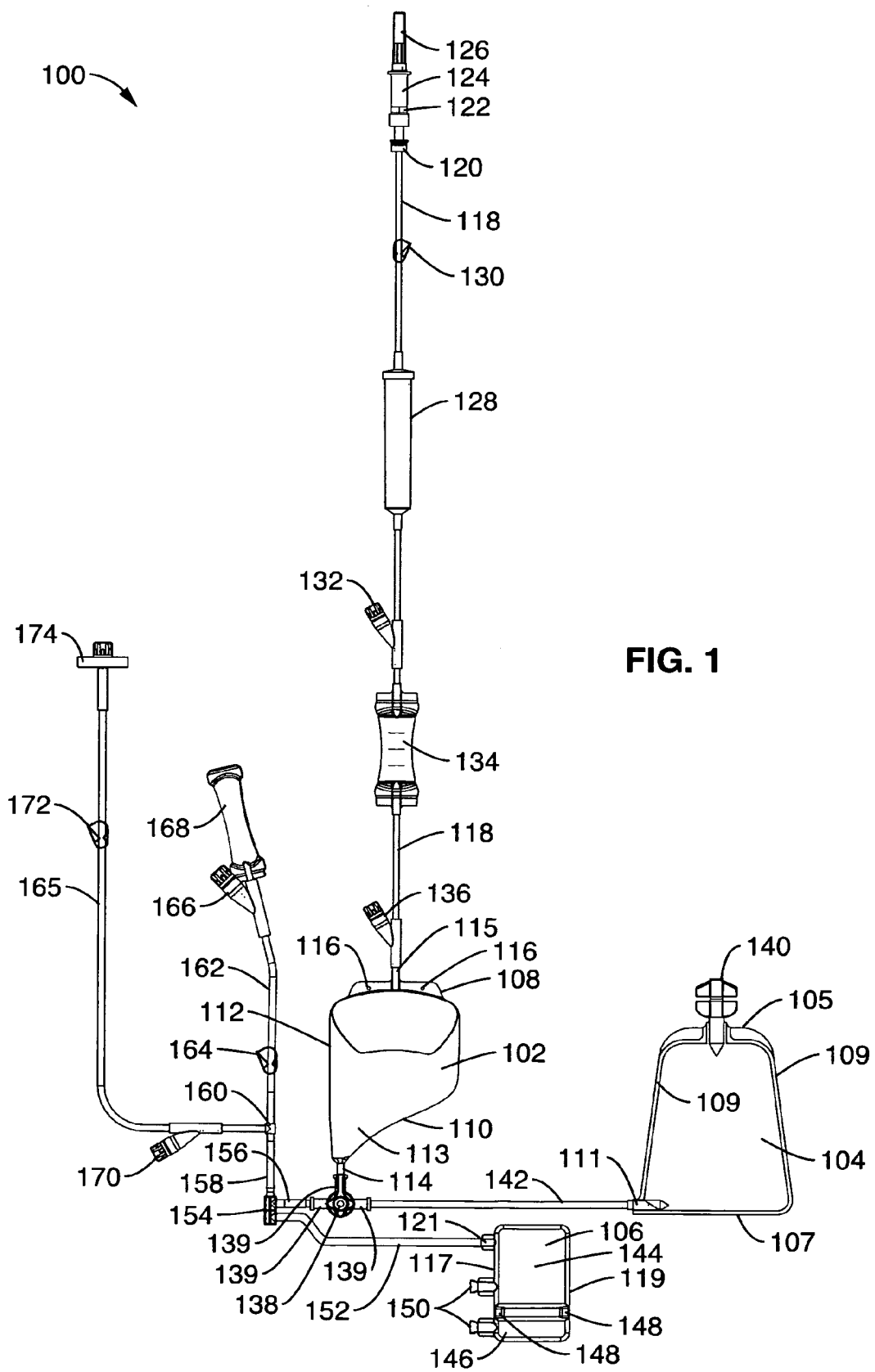
FIG. 1 is a two-dimensional lay-out of an embodiment of the bag set of the invention.

FIGS. 1 and 2 show an embodiment of bag set 100. Bag set 100 is functionally closed and preferably disposable. Bag set 100 includes three or more bags connected by lines or tubing to a metering valve, with inlet lines, clamps, filters, and sampling sites. Bag set 100 preferably includes three bags: processing bag 102, red blood cell (RBC) concentrate bag 104, and stem cell bag 106.

Processing bag 102 may be made of ethylene vinyl acetate (EVA), but may also be made of PVC or other plastics. RBC concentrate bag may be made of PVC or other plastics. Stem cell bag 106 may be made of EVA, although other plastics may be used. Bags 102 and 106 may be blow-molded. RBC concentrate bag may be RF welded, although it may be blow-molded.

Processing bag 102 is a three-dimensional bag that may have an asymmetric shape, including top edge 108, curved side 110, straight side 112, tapered bottom 113, and bottom outlet 114. Top edge 108 includes inlet 115 and two holes 116. Alternatively, processing bag 102 may be shaped symmetrically such that its sides taper symmetrically towards bottom outlet 114. The total volume of processing bag 102 may be about 240 mL, although in use, it is typically filled with about 50-150 mL of bone marrow or cord blood. Processing bag 102 is supplied through inlet line 118 which connects to inlet 115. Inlet line 118 includes a female luer 120 which allows bag set 100 to be connected to a syringe containing the bone marrow or cord blood to be transferred into processing bag 102. Female luer 120 is connected to male luer 122 which is connected to spike 124, which is covered by cap 126, which allows bag set 100 to be connected to a collection bag containing the bone marrow or cord blood to be transferred into processing bag 102. Inlet line 118 includes clot and bone chip filter 128 (about 200-300μ mesh). Line or tubing clamp 130 is located between clot and bone chip filter 128 and female luer 120. Inlet line 118 may optionally also include sampling site 132, sampling pillow 134, and sampling site 136, all located below clot and bone chip filter 128. Sampling sites 132 and 136 each include a needleless female luer and a non-breathing luer cap. Bottom outlet 114 directs output from processing bag 102 into metering valve 138.

RBC concentrate bag 104 may be a flat bag, having top edge 105, bottom edge 107, and two side edges 109, and includes butterfly spike port 140 which is used to remove an aliquot of the RBCs at the end of the process should that be desired. Bottom edge 107 includes inlet 111 at one corner. The volume of RBC concentrate bag 104 is about 100 mL, although in use, it is typically filled with about 30-80 mL. RBC concentrate bag 104 is connected at inlet 111 to supply line 142 which is connected to metering valve 138 at one of metering valve 138's connectors 139.

Stem cell bag 106 is a three-dimensional bag that is rectangular in shape. Stem cell bag 106 includes top edge 117, bottom edge 119, large compartment 144, and small compartment 146, with compartments 144 and 146 connected by two channels 148. Top edge 117 includes inlet 121 and two spike ports 150, which are used to remove the stem cells at the end of the process. The volume of stem cell bag 106 is about 30 mL, although in use, it is typically filled with about 25 mL, with about 20 mL in large compartment 144 and about 5 mL in small compartment 146. Stem cell bag 106 is connected at inlet 121 to stem cell bag inlet line 152 which is connected to supply line 156 through F connector 154. Supply line 156 is connected to metering valve 138 at one of metering valve 138's connectors 139. F Connector 154 connects supply line 156 and stem cell bag inlet line 152 to branch line 158. Branch line 158 is connected to sampling line 162 and cryoprotectant supply line 164 through T connector 160. Sampling line 162 includes line clamp 164 and sampling site 166, and terminates in sampling pillow 168. Cryoprotectant supply line 164 includes sampling site 170 and line clamp 172, and terminates in sterile filter 174 (preferably about 0.2μ mesh). Sampling sites 166 and 170 each include a needleless female luer and a non-breathing luer cap.

Lines 118, 142, 156, and 162 are tubing which may be made of PVC, EVA or other material. Lines 152 and 158 are tubing made of EVA. Cryoprotectant supply line 164 is co-extruded tubing made with PVC on the outside and EVA on the inside. Because plastic materials that come into contact with the cryoprotectant could, if they leach out into the cryoprotectant, enter stem cell bag 106 and contaminate the final product, it is advantageous to use a material, such as EVA, that does not contain plasticizers that could leach into the cryoprotectant for the lines that will be in contact with the cryoprotectant.

Figure 4A:
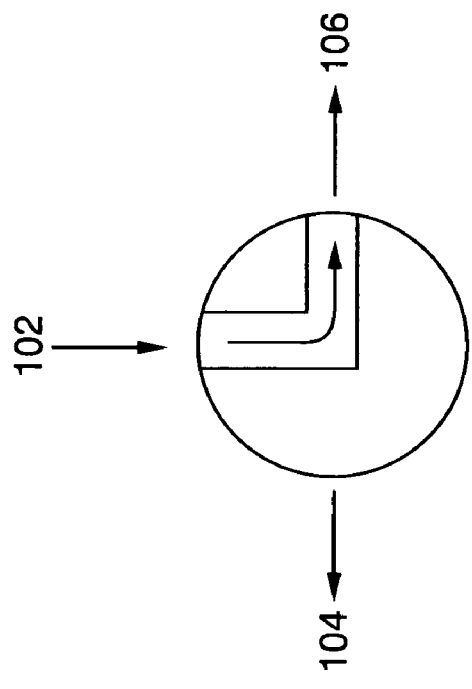
FIG. 4A is a schematic diagram showing one fluid path of an embodiment of the metering valve different from the embodiment of FIGS. 3A-3C.
Figure 4B:
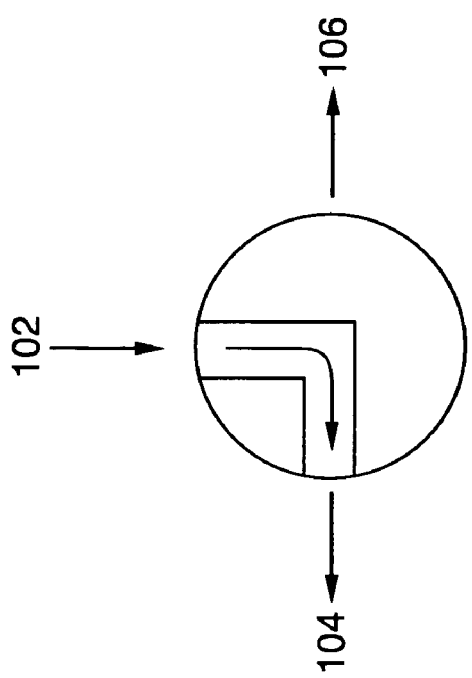
FIG. 4B is a schematic diagram showing a second fluid path of the metering valve shown in FIG. 4A.
Figure 5:
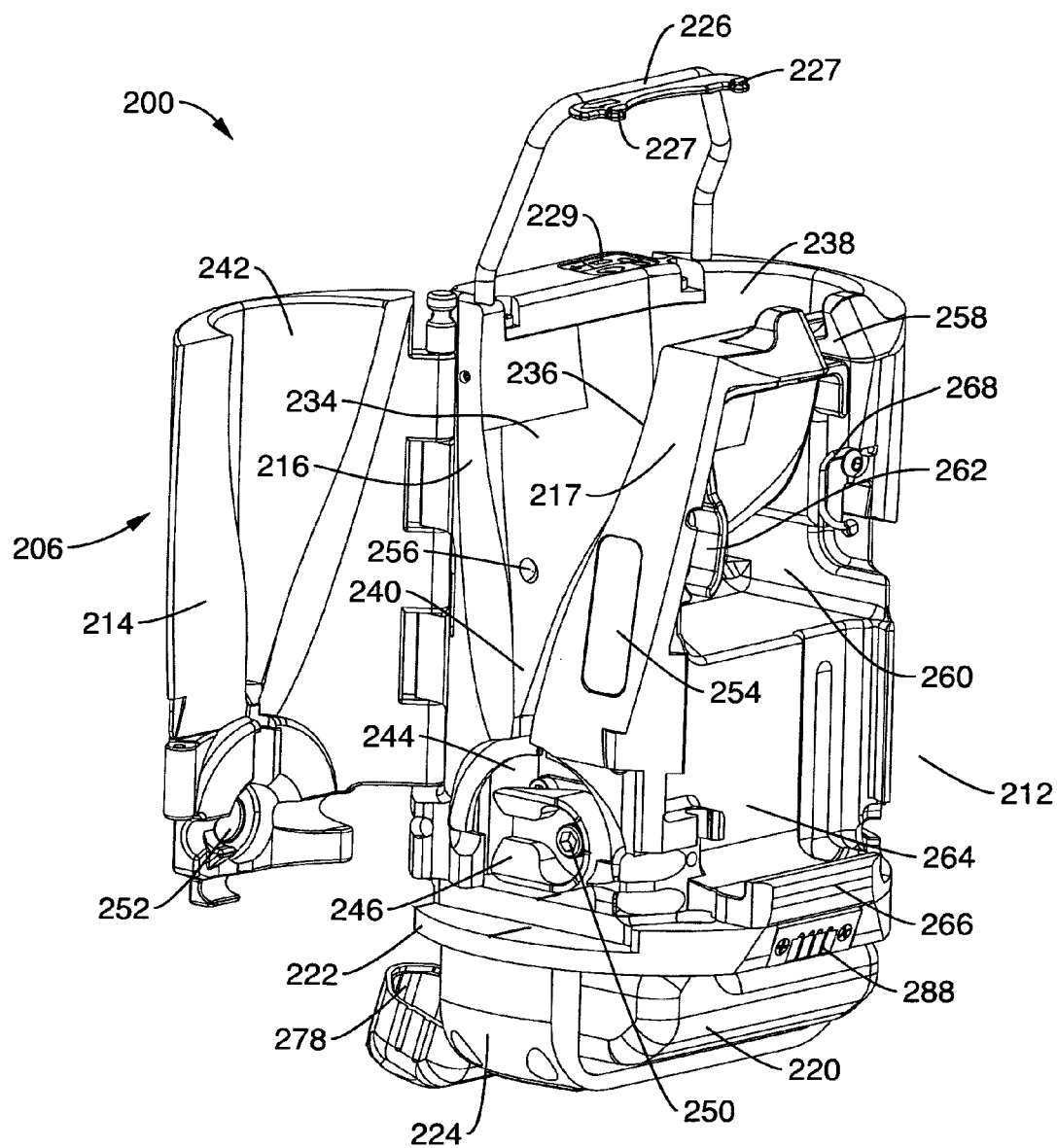
FIG. 5 is a perspective view of an embodiment of the processing device of the invention.
Figure 6:
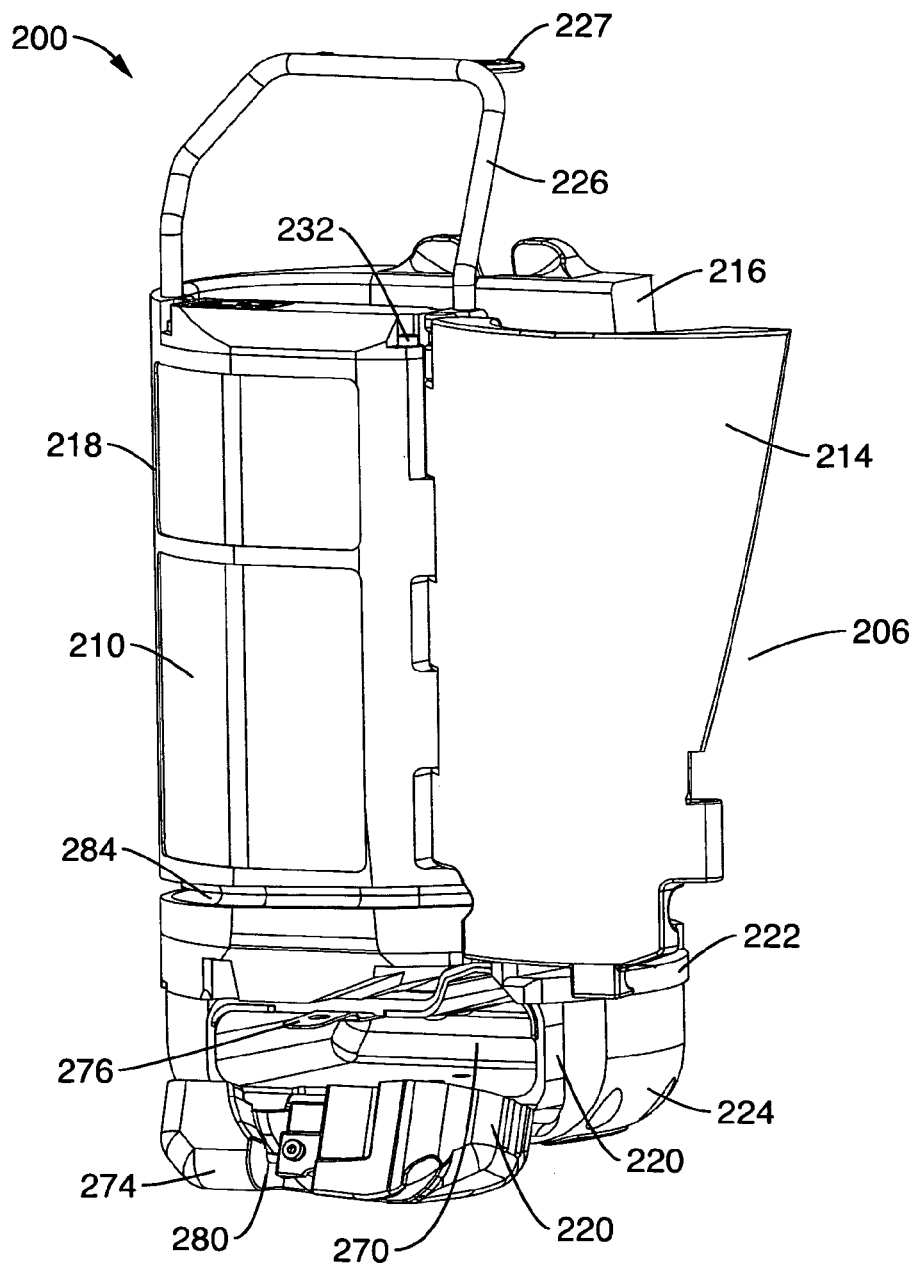
FIG. 6 is a perspective view of the processing device of FIG. 5.
Figure 7:
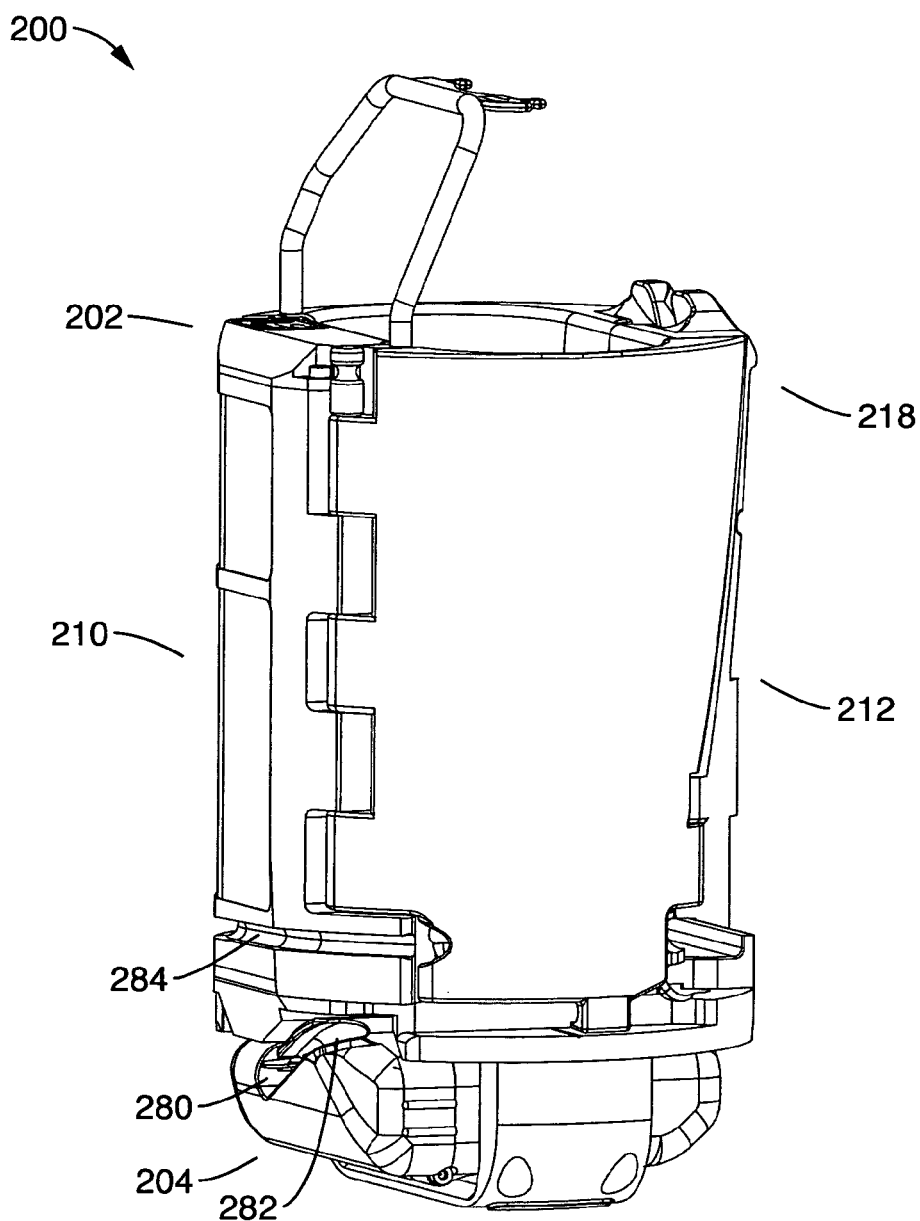
FIG. 7 is a perspective view of the processing device of FIG. 5.
Figure 8:
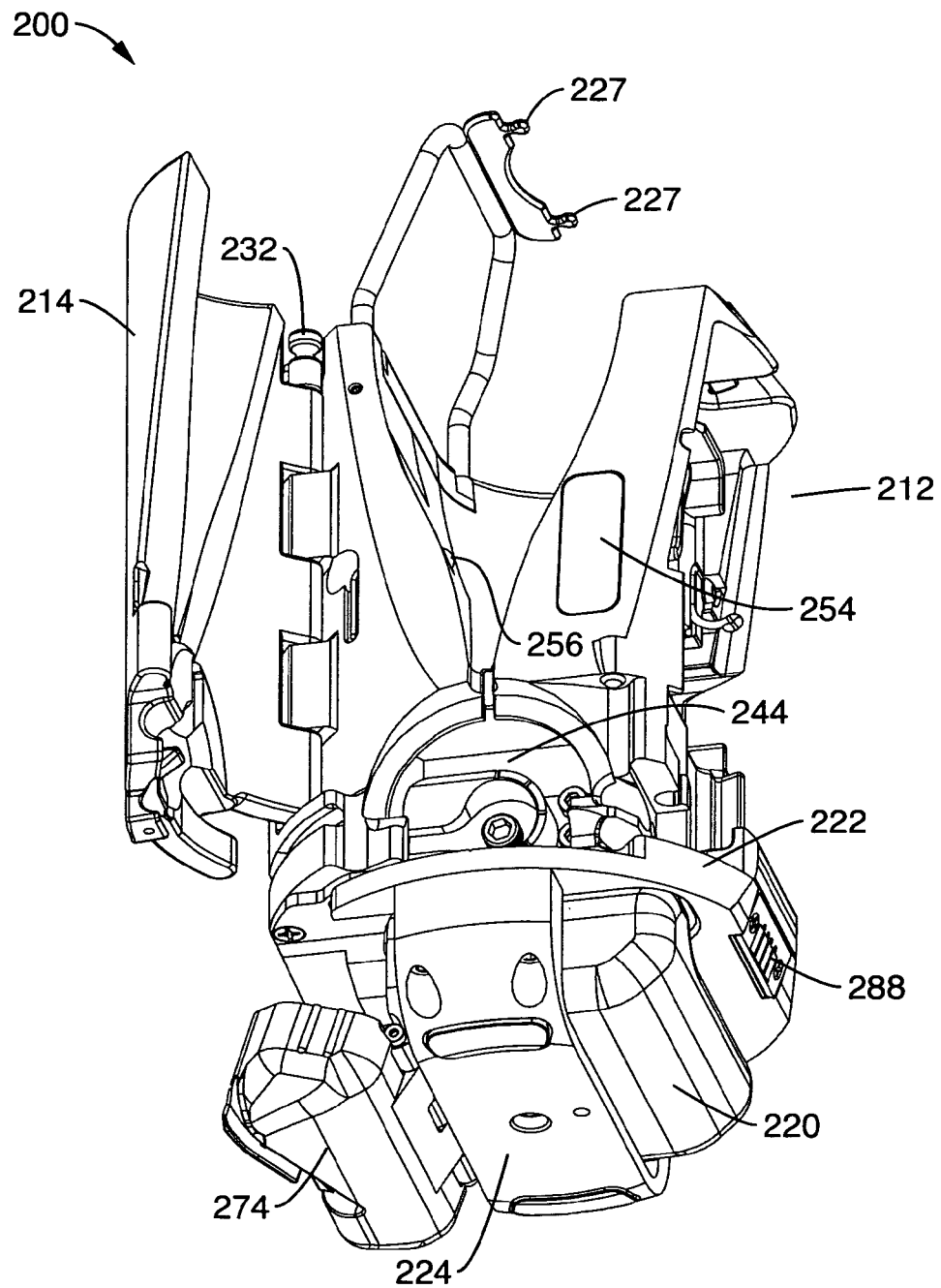
FIG. 8 is a perspective view of the processing device of FIG. 5.
Figure 9:
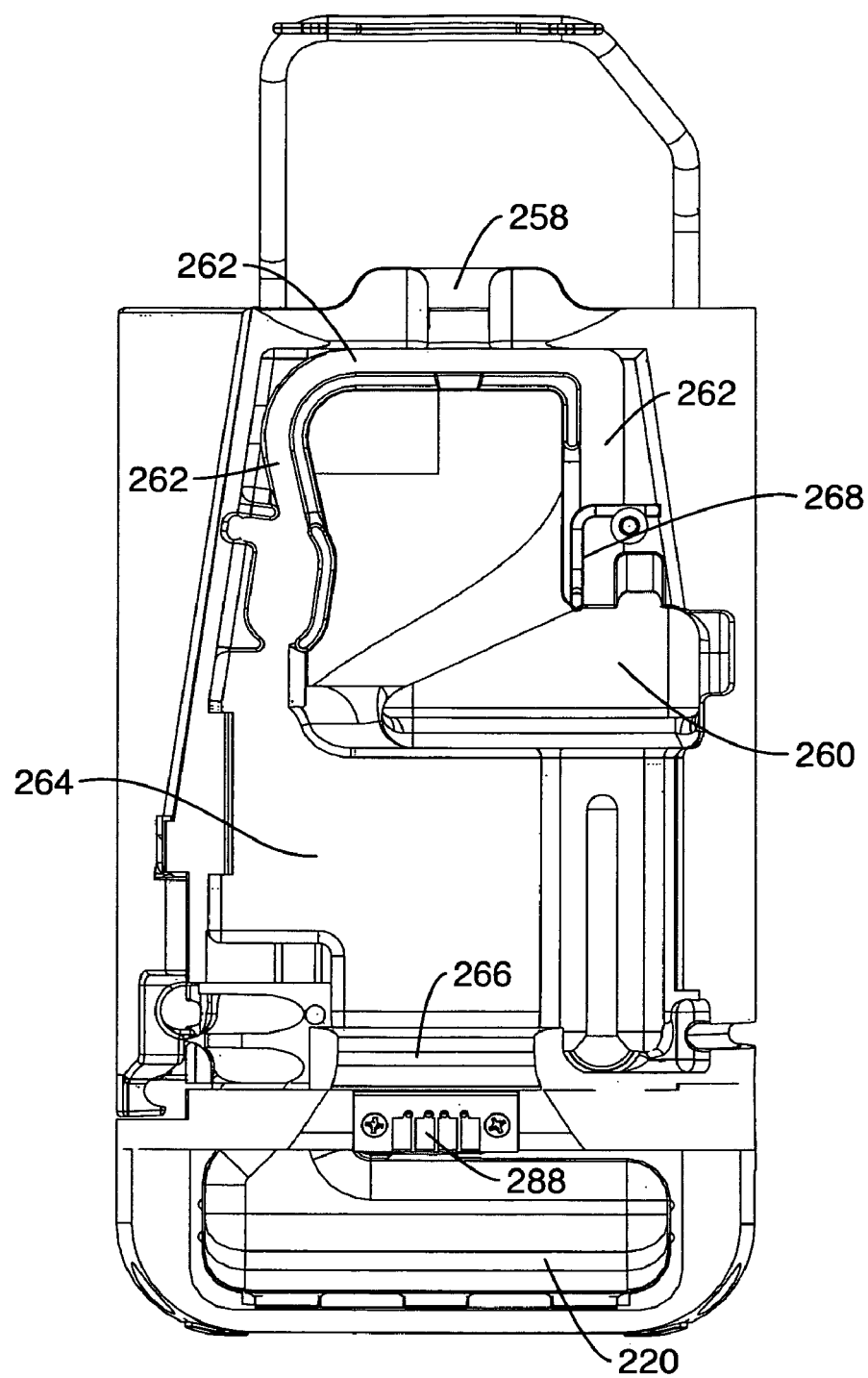
FIG. 9 is a side view of the processing device of FIG. 5.

Metering valve 138 may be a stopcock. In an embodiment, metering valve 138 is a three-way stopcock in that it has three connectors 139 such that it can be connected to three bags: processing bag 102, RBC concentrate bag 104, and stem cell bag 106. Other types of metering valves or stopcocks will also work, such as a four-way stopcock having four connectors. Metering valve 138 includes an outer portion 141 having three connectors 139 and an inner portion 143. Outer portion 141 may be made of polycarbonate. Inner portion 143 includes handle 145 and barrel 147, integrally molded, which may be made of polyethelene. Barrel 147 moves between several positions, including a closed position, defined as a position that does not allow any fluid flow through metering valve 138, and two open positions defined as positions that permit fluid flow through metering valve 138. The two open positions include one that permits fluid flow from processing bag 102 through metering valve 138 to RBC concentrate bag 104 and one that permits fluid flow from processing bag 102 through metering valve 138 to stem cell bag 106. In one embodiment, shown in FIGS. 3A-3C, barrel 147 of metering valve 138 may be configured to contain three openings, permitting fluid flow along three possible fluid paths: an intended path from processing bag 102 to RBC concentrate bag 104 as shown in FIG. 3A; an intended path from processing bag 102 to stem cell bag 106 as shown in FIG. 3B; and an unintended transient path between RBC concentrate bag 102 and stem cell bag 106 as shown in FIG. 3C that may occur when metering valve 138 is moving between its two intended positions. Such transient fluid flow is undesirable as it could allow some additional RBCs to flow into stem cell bag 106, thereby reducing the purity of the resulting stem cell composition. To address this concern, in another embodiment, shown in FIGS. 4A-4B, barrel 147 of metering valve 138 may alternatively be configured to contain only two openings, permitting fluid flow along only two possible fluid paths: an intended path from processing bag 102 to RBC concentrate bag 104 as shown in FIG. 4A; and an intended path from processing bag 102 to stem cell bag 106 as shown in FIG. 4B. This configuration would preclude any possible transient fluid flow between RBC concentrate bag 104 and stem cell bag 106. Metering valve 138 should be able to withstand the high pressures that occur during centrifugation; for example, a valve rated to about 500 psi is satisfactory. Supply line 142 leads from metering valve 138 to RBC concentrate bag 104. Supply line 156 leads from metering valve 138 to F connector 154, which leads to stem cell bag 106 via stem cell bag inlet line 152. Lines 142, 152, and 156 may each be heat sealed and separated from bag set 100.

If more bags are needed to separate additional components from the bone marrow or cord blood, bag set 100 may include additional bags. If additional bags are included, metering valve 138 will have additional connectors to accommodate each bag and the bag set will include additional supply lines to connect the metering valve to each bag. For example, if it is desired to separate the last portion of the RBCs in processing bag 102 from those RBCs transferred into RBC concentrate bag 104, a fourth bag is used. The fourth bag is connected to metering valve 138 by a separate supply line. In that case, metering valve 138 would be a four-way stopcock having four connectors and would include a barrel that permits fluid flow from processing bag 102 to the each of the other three bags.

Figure 16:
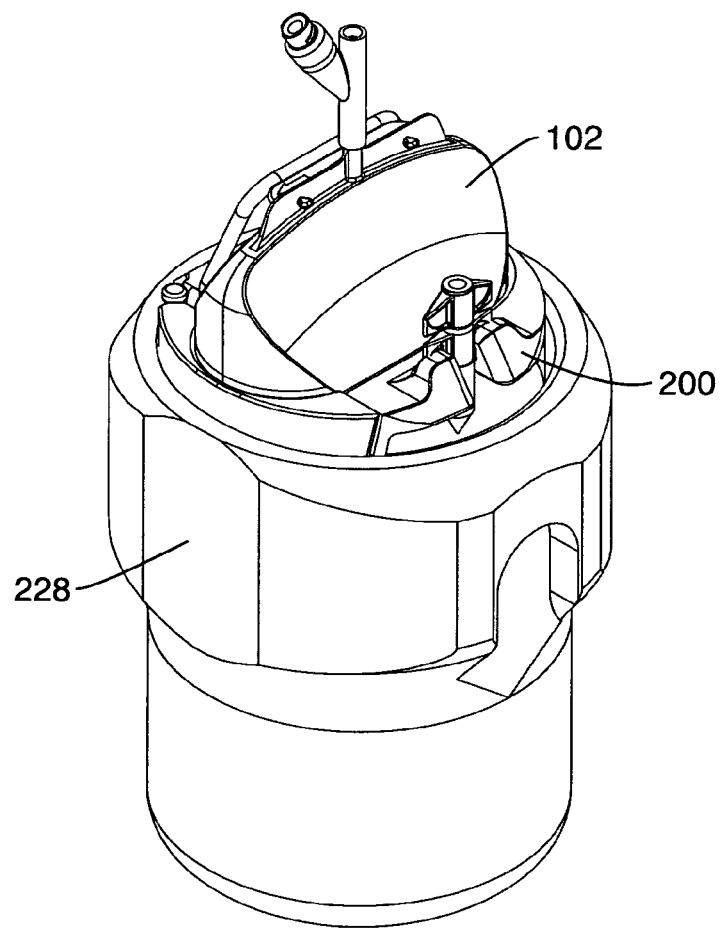
FIG. 16 is a perspective view of the bag set and processing device of FIG. 12 in a centrifuge bucket.
Figure 17:
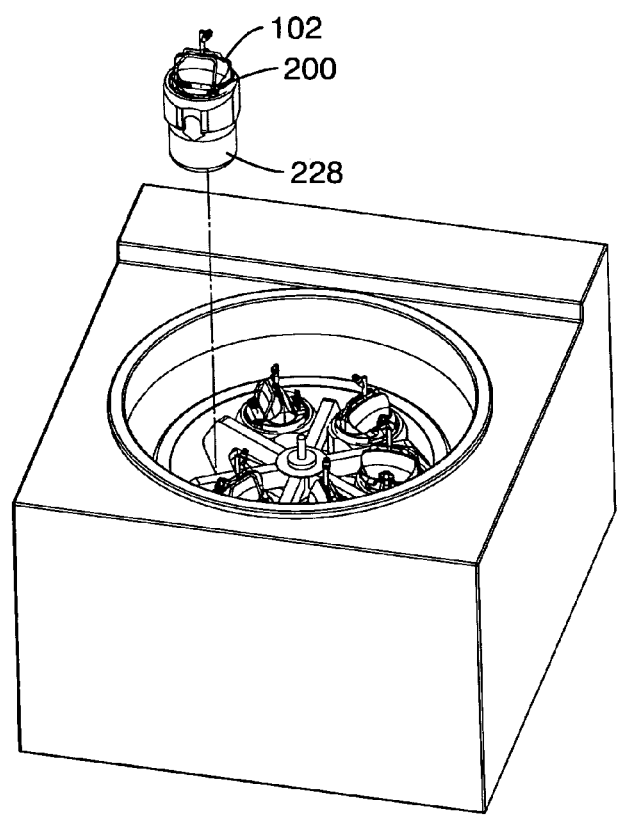
FIG. 17 is a partially exploded view showing the loaded centrifuge bucket of FIG. 16 and a centrifuge.

FIGS. 5-15 show an embodiment of processing device 200. Processing device 200 is somewhat cylindrical, having top 202, bottom 204, front 206, back 208, side 210, and side 212. Front 206 includes front door 214 and front walls 216 and 217. Processing device 200 has body 218, stem cell bag compartment 220, base plate 222, support bracket 224, and processing bag hanger 226. Body 218 and stem cell bag compartment 220 are preferably made of molded urethane, although other thermoplastic materials may be used. Base plate 222 is preferably made of stainless steel. Support bracket 224 is preferably made of aluminum. Processing bag hanger 226 is preferably made of stainless steel. Processing device 200 is sized to fit inside a centrifuge bucket with a minimum capacity of 1L, which may be circular or oval in cross-section. FIG. 16 shows processing device 200, containing bag set 100, inside a centrifuge bucket 228. FIG. 17 shows how a loaded centrifuge bucket 228 fits into a centrifuge with five other loaded centrifuge buckets already in place.

Body 218 of processing device 200 includes main compartment 230, which has an elongated oval shape dimensioned to receive processing bag 102. Main compartment 230 is open at the top and is accessed by opening front door 214 which is attached to front 206 of processing device 200 by hinge 232. Main compartment 230 has side walls 234 and 236 and back wall 238 that conform to and support processing bag 102, and tapers down to channel 240, which is dimensioned receive tapered bottom 113 of processing bag 102. Side walls 234 and 236 cradle processing bag 102 loosely around the middle and more tightly at tapered bottom 113. Closer tolerance near tapered bottom 113 of processing bag 102 is advantageous in order to provide support for processing bag 102 and its contents during the high pressures of centrifugation and to minimize disturbance to the contents of the bag. Front door 214 includes a concave inner recess 242 on its inside surface that corresponds to side walls 234 and 236 and channel 240 of main compartment 230 and provides a continuous surface, such that when front door 214 is closed it conforms to and supports processing bag 102.

Recess 244 is located on front 206 of processing device 200 below front walls 216 and 217, and is configured to support metering valve 138's connectors 139. Valve actuator cuff 246 is located inside recess 244, and is sized and configured to receive metering valve 138's handle 145. Valve actuator cuff 246 is attached to the shaft of servo motor 248 by screw 250. A corresponding recess 252 is located on the inside of front door 214 and is sized and configured to receive the protruding end and connectors 139 of metering valve 138.

One or more optical sensors 254 are assembled through front wall 217 of main compartment 230, having their apertures located on side wall 236, with an equal number of LEDs 256 located on opposite side wall 234. LED 256 includes a red LED light, although other types of LEDs may be used. One optical sensor 254 and one LED 256 are preferably located about 2 cm above channel 240 such that the volume in processing bag 102 between the level of optical sensor 254 and LED 256 and the level of metering valve 138 is about 2 mL, although other distances and corresponding volumes may also be used. If additional optical sensors and LEDs are included, they may be located above or below optical sensor 254 and LED 256, depending on the desired volumes of RBCs to be separated.

Side 212 of processing device 200 includes notch 258, storage cavity 260, channel 262, RBC concentrate bag recess 264, support shelf 266, and hook 268. Notch 258 is sized and configured to receive spike port 140 of RBC concentrate bag 104. RBC concentrate bag recess 264 extends from notch 258 down to support shelf 266, and is sized and configured to receive RBC concentrate bag 104. Storage cavity 260 is located below notch 258 and is behind and continuous with RBC concentrate bag recess 264. Channel 262 extends along the inside edges of RBC concentrate bag recess 264, adjacent to front door 214, top 202, and back 208. Support shelf 266 is a horizontal shelf which forms the floor of RBC concentrate bag recess 264.

Stem cell bag compartment 220 is a horizontal, hollow rectangular compartment having a larger side 270 located under hinge 232 of front door 214. Stem cell bag compartment 268 is located below base plate 232 and is attached to load cell 272. Stem cell bag compartment 220 is accessed through hinged door 274 which opens downward, and snaps into place via latch 276 located inside stem cell bag compartment 220 at its top edge. The inside of hinged door 274 contains recess 278 that is sized and configured to accommodate stem cell bag 106's spike ports 150 and inlet 121. The outside of hinged door 274 contains slot 280 and channel 282 sized to accommodate stem cell bag inlet line 152.

Bottom channel 284 extends above and parallel to base plate 222, from front 206 under hinge 232 across side 210 and back 208 to side 212. Bottom channel 284 is sized to accommodate line 142.

Processing device 200 includes processing bag hanger 226 that extends above top 202 at side 210. Processing bag hanger 226 has tabs 227 that engage holes 116 on processing bag 102, maintaining processing bag 102 in position inside processing device 200. LED windows 229 are located on top 202 at side 210.

Support bracket 224 is a U-shaped bracket that is attached to base plate 222 by screws 225 and is oriented parallel to processing device 200's sides 210 and 212.

Figure 10:
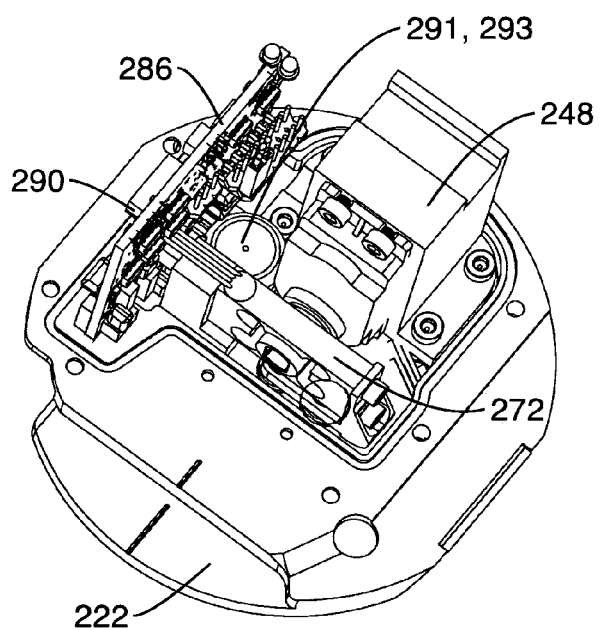
FIG. 10 is a perspective view of an embodiment of the base plate of the processing device of the invention, showing the components.
Figure 11:
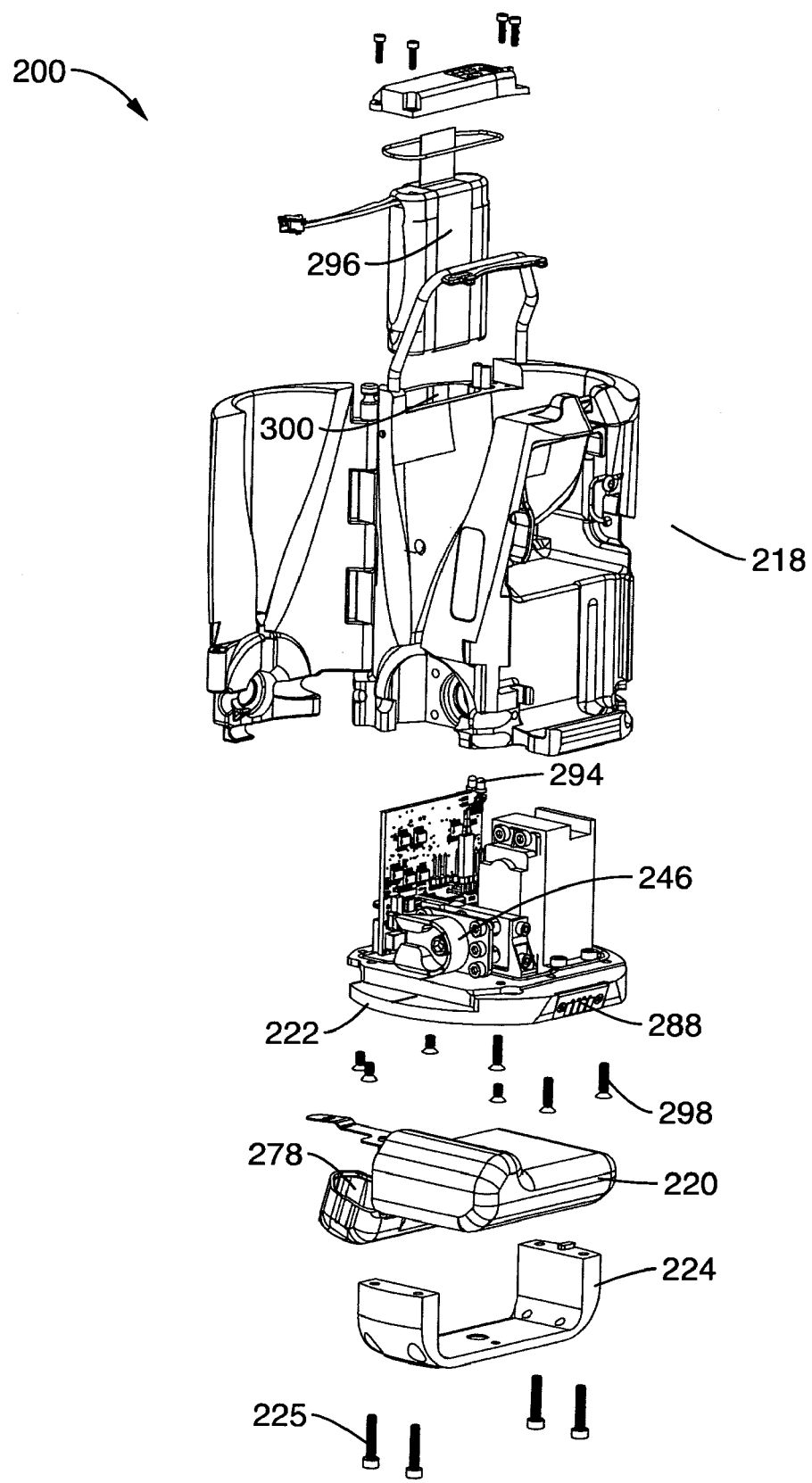
FIG. 11 is an exploded view of the processing device of FIG. 5.
Figure 12:
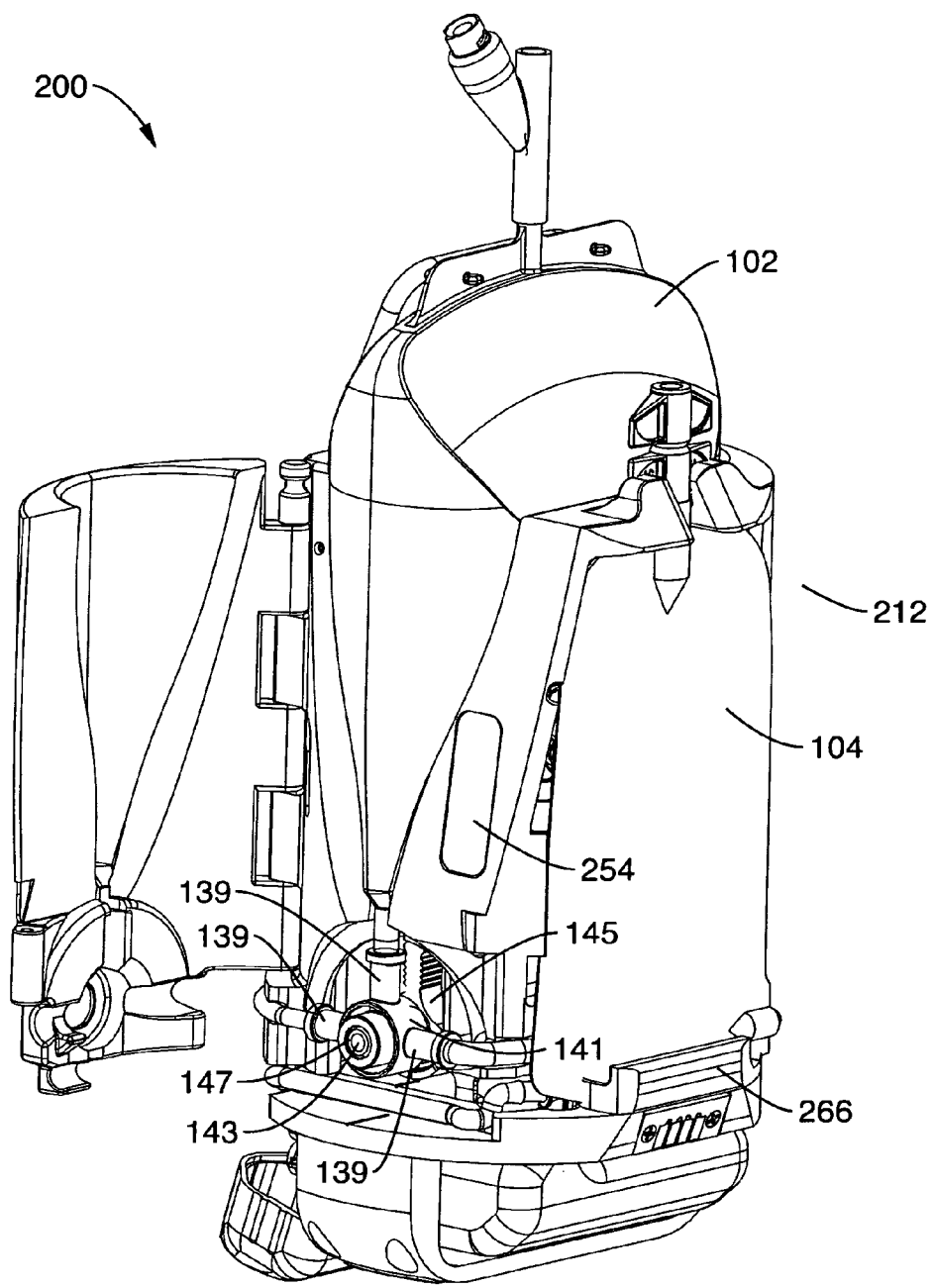
FIG. 12 is a perspective view of the bag set of FIG. 1 placed in the processing device of FIG. 5.
Figure 13:
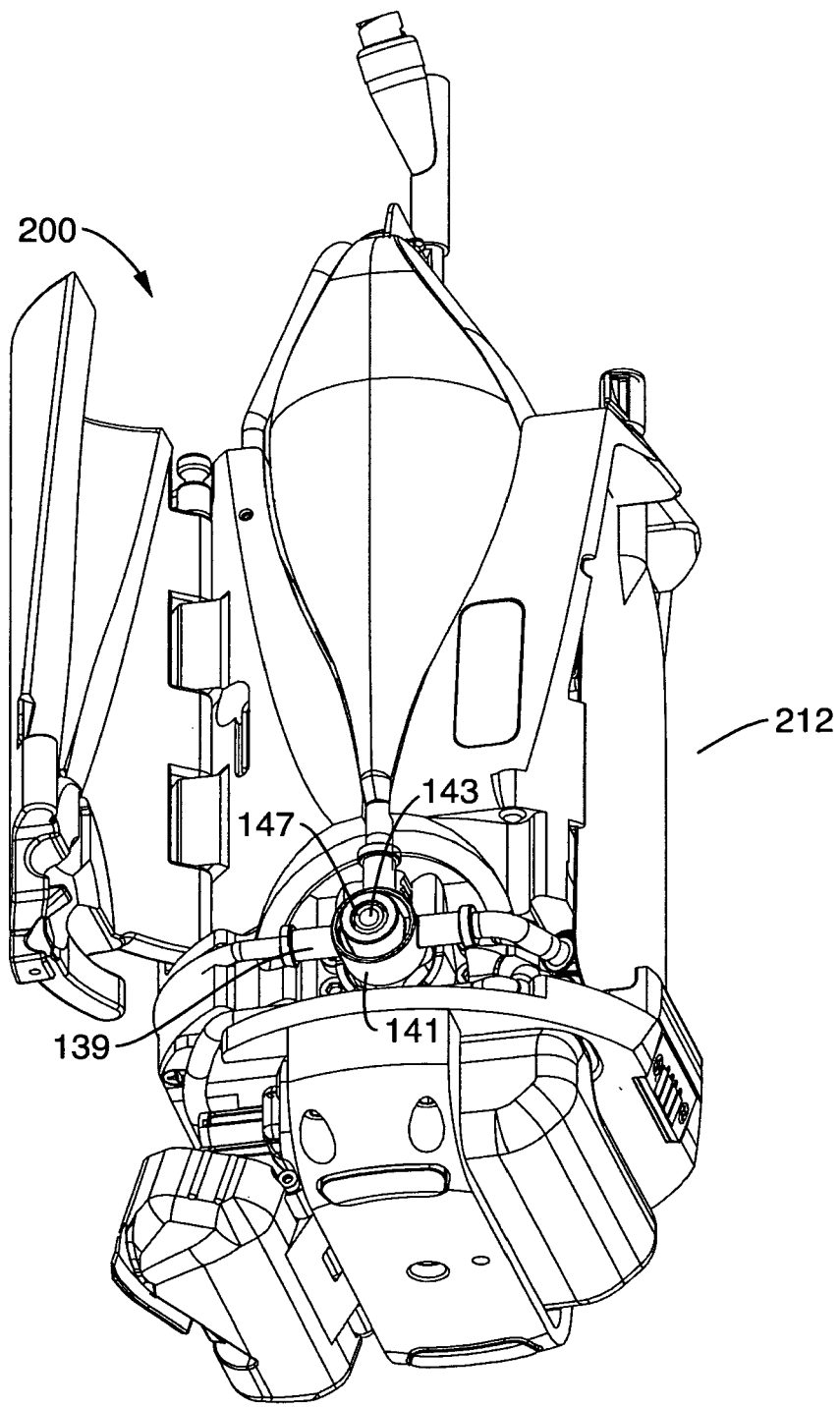
FIG. 13 is a perspective view of the bag set and processing device of FIG. 12.
Figure 14:
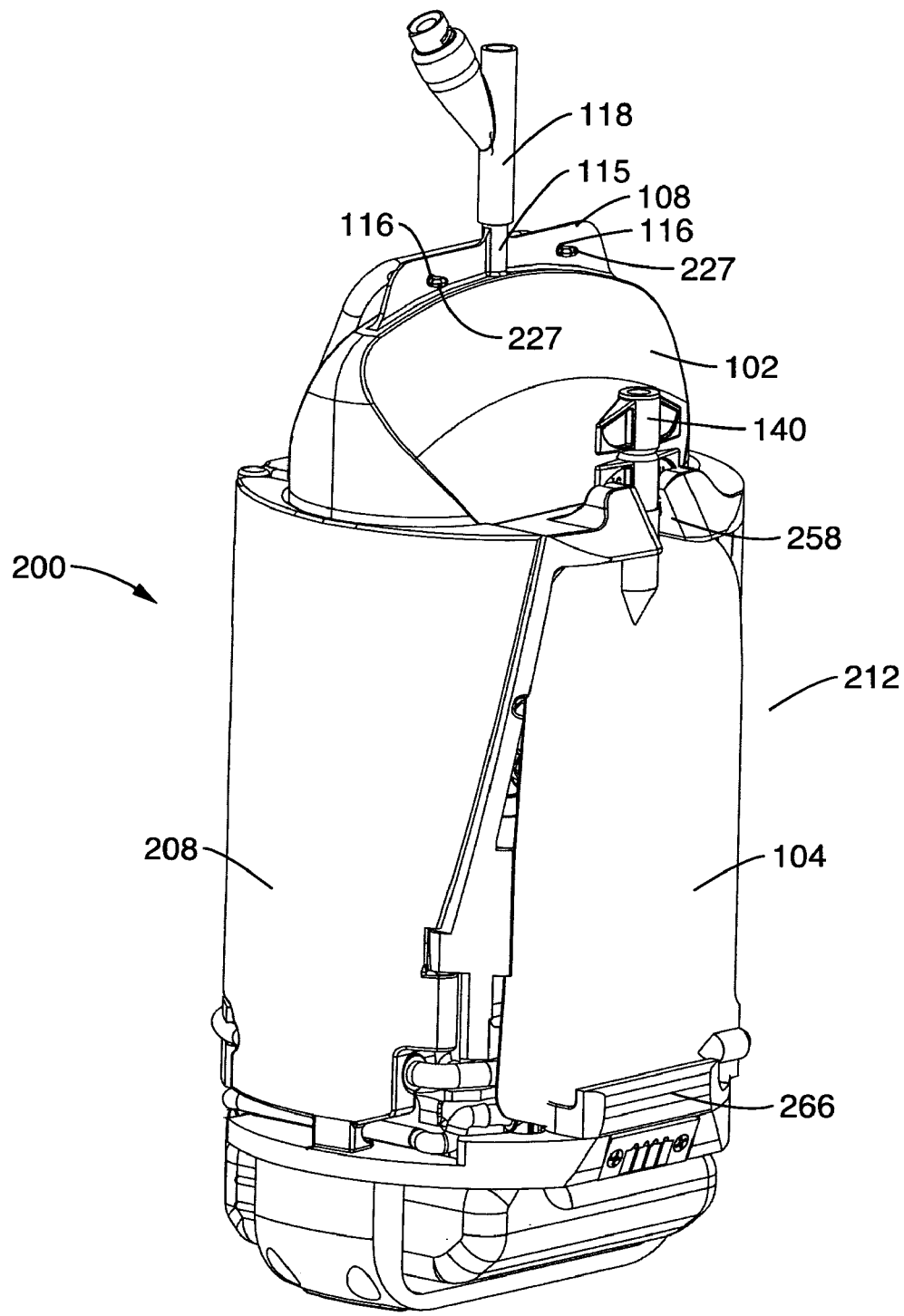
FIG. 14 is a perspective view of the bag set and processing device of FIG. 12.
Figure 15:
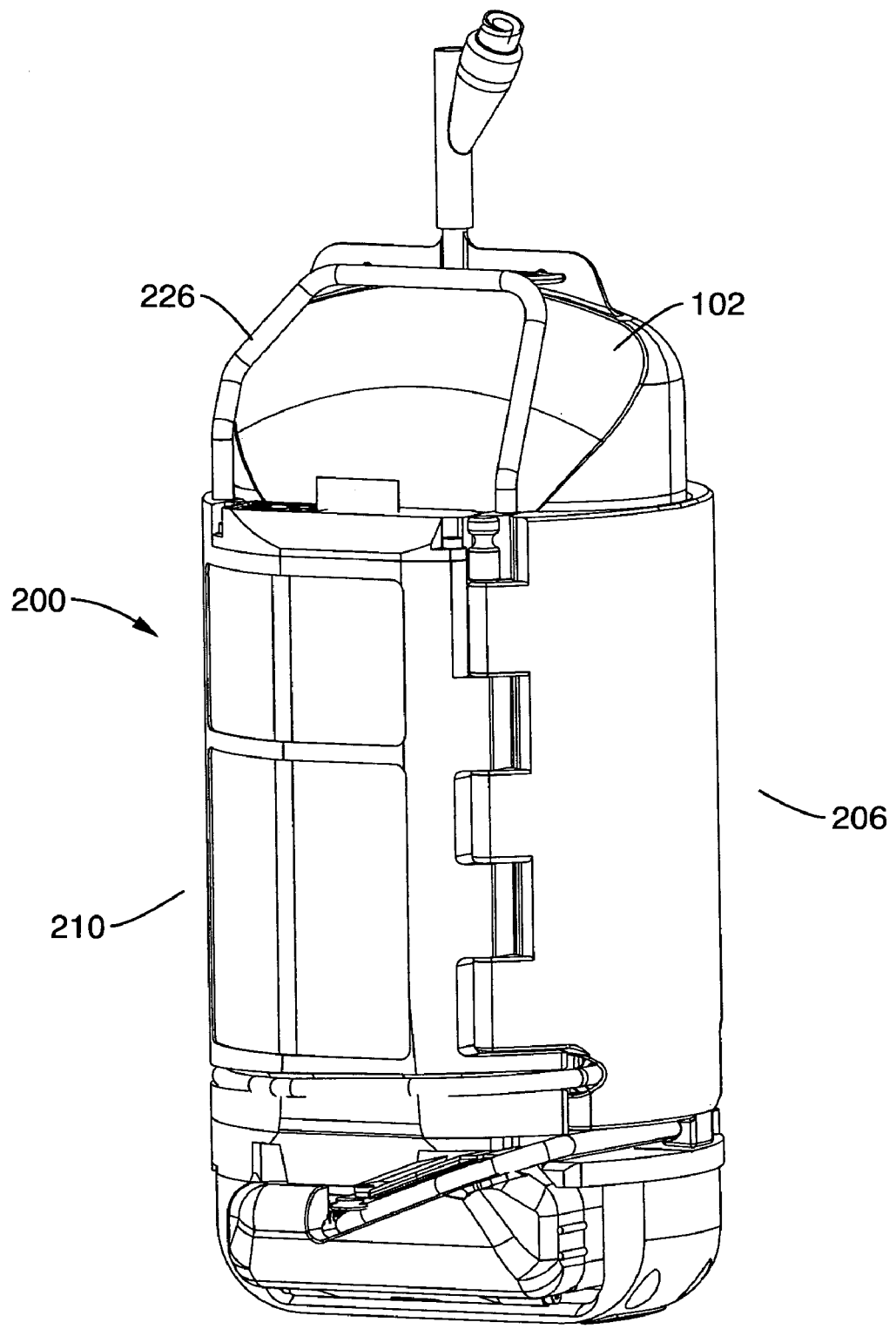
FIG. 15 is a perspective view of the bag set and processing device of FIG. 12.

As shown in FIG. 10, base plate 222 preferably has the following components mounted to it: printed circuit board 286, servo motor 248, load cell 272, and interface contact printed circuit board 288. Printed circuit board 286 contains programmable read only memory microcontroller 290. Microcontroller 290 may require temperature compensation due to heat generation during centrifugation. Load cell 272 is a temperature compensated strain guage load cell. Servo motor 248 is a gear reduction motor. One or more accelerometers 292 are mounted on printed circuit board 286; if two accelerometers 292 are used, one may be mounted on top of the other. Preferably, accelerometers 292 include a low g accelerometer 291 which measures about 0-200×g and a high g accelerometer 293 which measures about 1000-1700×g. Printed circuit board 286 also includes status LEDs 294 that are visible through LED windows 229. One or more status LEDs 294 may indicate the charge status of battery 296 and the current step being performed in the process, as well as other information. Interface contact printed circuit board 288 is provided to connect to an external battery charger and to provide a communication connection with a personal computer. Base plate 222 is attached to body 218 by screws 298.

Figure 18:
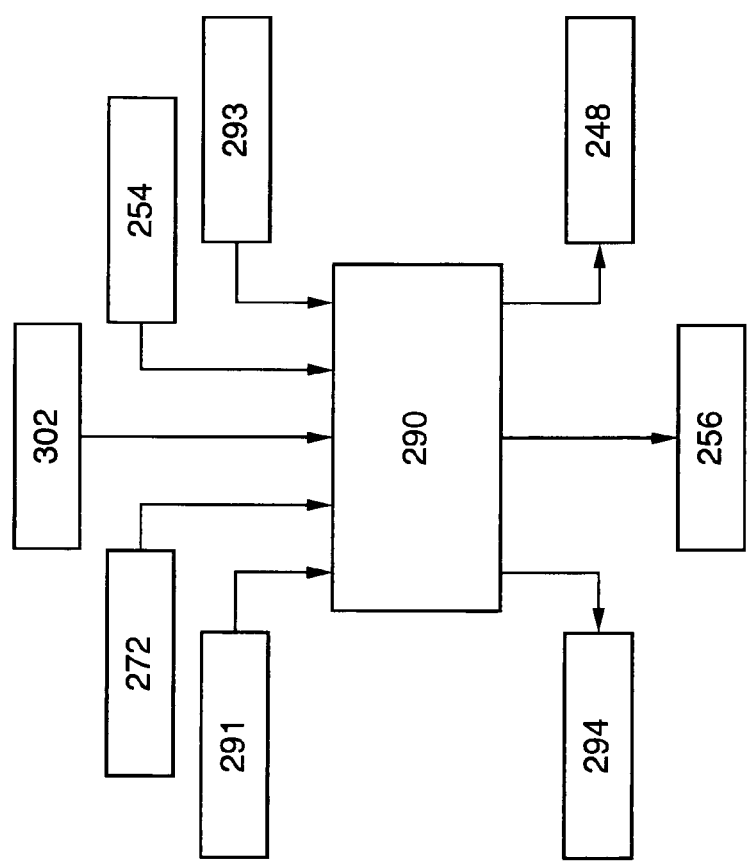
FIG. 18 is a block diagram of the inputs and outputs of the microcontroller of the processing device of FIG. 5.

FIG. 18 is a block diagram showing the inputs and outputs of microcontroller 290. Optical sensor 254, battery voltage 302, load cell 272, and accelerometers 291 and 293, generate analog outputs which are converted to digital inputs received by microcontroller 290. Microcontroller 290 records, stores, and analyzes those inputs at predetermined timed intervals. Microcontroller controls servo motor 248, LED 256 for optical sensor 254, and status LEDs 294. When bag set 100 including metering valve 138 is properly placed into processing device 200, servo motor 248 is connected through its drive shaft to valve actuator cuff 246 and, in response to a signal from microcontroller 290, servo motor 248 causes metering valve 138 to move to different positions to open or close fluid flow to the bags of bag set 100.

Battery 296 is located in battery cavity 300 on top 202 at side 210 of processing device 200. Battery 296 is a rechargeable nickel metal hydride battery including three cells with a total of about 3.8-4 volts, which voltage is regulated to provide a constant voltage of 5 volts. Battery 296 powers microcontroller 290, optical sensor 254, accelerometers 291 and 293, load cell 272, optical sensor LED 256, status LEDs 294, servo motor 248, and all electrical circuitry in processing device 200 including communication with a personal computer.

Processing unit 200 may be placed in a separate docking station which includes a battery charger and which may be connected to a personal computer. Data from microcontroller 290 may be transferred to the personal computer, and commands may be received from the personal computer, via the docking station through interface contact printed circuit board 288.

As shown in FIGS. 12-15, bag set 100 is inserted into processing device 200 as follows. Stem cell bag 106 is placed into stem cell bag compartment 220 such that bottom edge 119 fits in first, and small compartment 146 is folded over and placed in larger side 270. Inlet 121 and spike ports 150 are placed inside recess 278 of hinged door 274. Stem cell bag inlet line 152 is placed in slot 280 of hinged door 274. Hinged door 274 is then closed and latched with latch 276. Stem cell bag inlet line 152 is placed in channel 282. Metering valve 138's handle 145 is placed into valve actuator cuff 246. Processing bag 102 is oriented in main compartment 230 such that front door 214 closes over processing bag 102's straight side 112. F connector 154 is placed inside RBC concentrate bag recess 264. Line clamp 165 is closed and placed inside channel 262 along with sampling line 162. Cryoprotectant supply line 165, line clamp 172 (closed), and sampling site 170 are placed into storage cavity 260, with sterile filter 174 placed into the right side wall receptacle of storage cavity 260. Sampling site 166 is anchored at hook 268. Sampling pillow 168 fits into recess directly below the filter receptacle in the right side of RBC concentrate bag recess 264. Then, supply line 142 is placed into bottom channel 284 and RBC concentrate bag 104 is placed into RBC concentrate bag recess 264. Inlet line 118 and sampling site 136 are folded downward and toward processing bag hanger 226 at side 210. Holes 116 of processing bag 102 are attached to hanger 226's tabs 227. Front door 214 is closed. Spike port 140 fits into notch 258, with bottom edge 107 on support shelf 266, such that RBC concentrate bag 104 fits over storage cavity 260. Branch line 158 is placed vertically along the left side of storage cavity 260.

Method of Recovering Stem and Progenitor Cell Composition from Bone Marrow or Cord Blood The method includes centrifugation which stratifies and separates the cells of the bone marrow or cord blood by cell density and size. The bone marrow or cord blood to be processed contains plasma, RBCs, WBCs, and stem cells, as indicated by the presence of CD34+ and ALDH Br+ stem cell markers. The resulting stem cell product is a composition of stem and progenitor calls which include some WBCs, and significantly reduced RBCs and plasma. The method, using the system described above, is performed in a sterile, functionally closed system capable of processing a range of volumes of bone marrow or cord blood and yields a final product whose volume may be selected in advance by the user. The method significantly reduces the volume of the bone marrow by removal of excess RBCs and plasma, and, if clinically advantageous, neutrophils and platelets, thereby concentrating the stem cells in the final stem cell composition. No xenobiotic additives are required for this method which recovers a high percentage of the stem and progenitor cells from the bone marrow or cord blood.

As used in this specification, the term "g force" refers to relative centrifugal force, and all references to specific g forces are determined at the location of optical sensor 254 in processing device 200. It should be understood that the specific g forces and time periods mentioned herein illustrate an embodiment of the method, and that g forces and time periods other than those mentioned are useful and are encompassed in other embodiments of the method.

In one embodiment of the method, the following steps are included.

1. The bone marrow or cord blood is transferred into the processing bag.

Bone marrow or cord blood is harvested or collected into a collection container such as a bag, syringe, or other container, preserved with an anticoagulant, such as heparin or CPD, and transferred into processing bag 102. The transfer may be accomplished by inserting spike 124 into the collection bag, attaching female luer lock 120 to the syringe, or sterile-docking the tubings of the collection bag and the processing bag using a sterile connection device. Line clamp 130 is open. The bone marrow or cord blood is then transferred by gravity flow from the collection container to processing bag 102 through inlet line 118. The bone marrow or cord blood passes through the clot and bone chip filter 128, which removes aggregates (such as blood clots, fat globules, and bone chips) from the bone marrow or cord blood before it reaches processing bag 102. After the bone marrow or cord blood is transferred, inlet line 118 is heat sealed above sampling site 132, and the collection container, clot and bone chip filter 128, and rest of line 118 are removed.

A volume of about 25-200 mL of bone marrow or cord blood may be placed into processing bag 102, with about 50-170 mL being preferred. If the original volume of collected bone marrow or cord blood is about 100 mL, and the bone marrow or cord blood has a hematocrit of about 30%, the RBC volume will be about 30 mL, the WBC and stem and progenitor cell volume will be about 1 mL, and the remaining volume will be plasma.

Unexpectedly, no sedimentation agent or other xenobiotic additives are necessary to perform this method and achieve the efficient recovery of stem and progenitor cell from bone marrow or cord blood as described herein. If a sedimentation agent, such as HES, is desired, it may optionally be added to the bone marrow in processing bag 102.

A sample of the bone marrow or cord blood to be processed may be taken from processing bag 102, if desired, after heat sealing inlet line 118 above sampling site 132. Sampling pillow 134 is squeezed and released to draw the sample into the pillow. Inlet line 118 is then heat sealed above sampling site 136, and sampling pillow 134 is removed, along with sampling site 132. The bone marrow or cord blood in sampling pillow 134 may then be accessed through sampling site 132 for separate assay, such as for cell counts, cell viability, microbial contamination, and HLA analysis.

If no sample is taken from processing bag 102, inlet line 118 is heat sealed above sampling site 136 and all components above sampling site 136 are removed.

2. The loaded bag set is placed into the processing device.

Bag set 100, including the bags, lines, and metering valve, is placed into processing device 200 as described above.

As shown in FIGS. 16 and 17, processing device 200 with bag set 100 is placed into a centrifuge bucket 228 of a centrifuge, which may be refrigerated. The centrifuge needs to be balanced, either with another processing device 200 or with suitable counterweights.

3. The bag set is centrifuged in the processing device at a sufficient g force and elapsed time to stratify the cells of the bone marrow or cord blood in the processing bag into layers based on their density and size.

Bag set 100 in processing device 200 is centrifuged at a pre-set g force and for a pre-set time sufficient to stratify the bone marrow or cord blood cell populations in processing bag 102 into layers by cell density and size. For example, centrifugation may be performed at about 1400×g for about 20 to about 40 minutes. During this stratification step, metering valve 138 is in its closed position such that no fluid flow is permitted through metering valve 138. Accelerometer 293 measures the g force during centrifugation.

Figure 19:
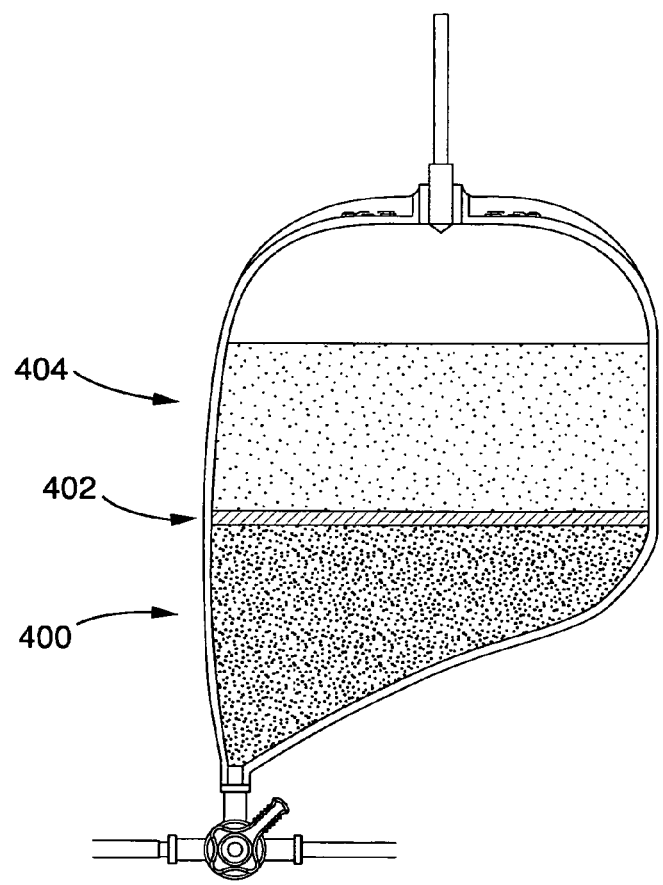
FIG. 19 is a partial cross-section side view of the processing bag of FIG. 1 showing the cell layers after the stratification step.

Centrifugation is preferably continued until the cells have been stratified into three layers. See FIG. 19 which shows processing bag 102 after this stratification step has been performed. The lower, most dense layer 400 is primarily RBCs; the middle layer 402 of intermediate density is the layer of WBC/stem and progenitor cells and some platelets; and the upper, least dense layer 404 is primarily plasma with some additional platelets. The percentage of platelets residing with the stem and progenitor cells will be greater as the duration of centrifugation increases. The 1400 g force and time of centrifugation of 20-40 minutes is sufficient to cause more than 70% of the stem cells to migrate to the WBC/stem and progenitor cell layer, although it is preferable for at least about 80% to 90% of the stem cells to be located in this layer.

4. The bag set is centrifuged in the processing device at a lower g force to allow separation and transfer of most of the RBCs from the processing bag into the RBC concentrate bag.

After the cells have been stratified in processing bag 102 in the previous step, bag set 100 in processing device 200 is centrifuged at a pre-set lower g force and for a pre-set time sufficient to allow separation and transfer of most of the RBCs from processing bag 102 into RBC concentrate bag 104. The g force is lower than the g force used in step 3 in order to allow the RBC layer to flow from processing bag 102 through metering valve 138 through supply line 142 into RBC concentrate bag 104 in a controlled manner with minimal risk of cell damage. For example, centrifugation may be performed at about 80×g for about three to about ten minutes. This centrifugation step may be continuous with the centrifugation of the previous stratification step, by automatically reducing the g force of the previous step to the pre-set lower g force, or it may be initiated and performed after the previous centrifugation step has been completed and come to a stop.

Accelerometer 291 measures the g force during centrifugation. As soon as microcontroller 290 receives input from accelerometer 291 that the pre-set g force is stable, for example, for about 30 seconds, microcontroller 290 directs servo motor 248 to cause valve actuator cuff 246 to cause metering valve 138 to open to the position which creates a fluid path from processing bag 102 through supply line 142 and into RBC concentrate bag 104. While metering valve 138 is open, most of the lower layer in processing bag 102, which consists of packed RBCs, flows into RBC concentrate bag 104.

Figure 20:
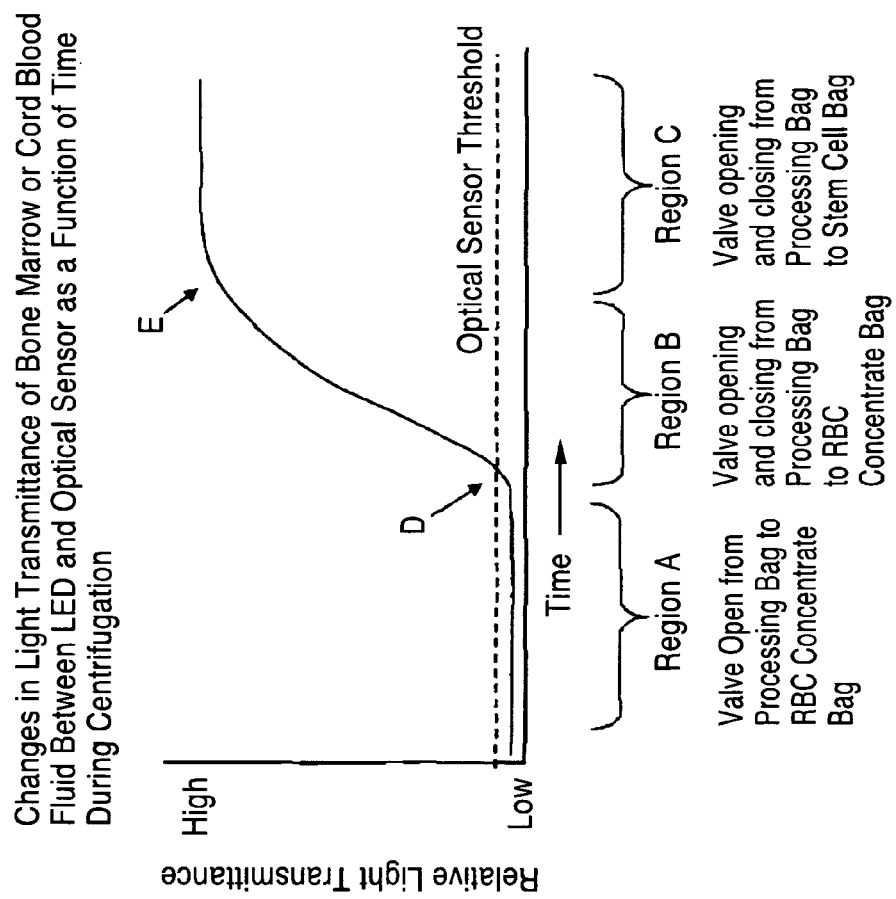
FIG. 20 is a graph showing the changes in light transmittance as a function of time during the centrifugation steps of the method.

Concurrently while metering valve 138 is open, microcontroller 290 directs optical sensor 254 to take readings of the transmittance of light from LED 256 through the bone marrow or cord blood in processing bag 102 as the fluid flows by LED 256. Microcontroller 290 continuously records and analyzes the light transmittance it receives as input from optical sensor 254 as a function of time. FIG. 20 shows the relative light transmittance as a function of time during centrifugation as the cell layers flow past LED 256 and optical sensor 254, beginning in step 4 after metering valve 138 opens and continuing through step 8, excluding optional step 5. The line approximates an S shaped curve, with region A, where there is little or no light transmittance and the line is almost horizontal; region B, where there is a rapid increase in the amount of light transmittance and the slope of the line is steep; and region C, where there is a high amount of light transmittance and the line is almost horizontal.

During this step, the RBC layer is flowing past optical sensor 254. Because the RBC layer has the greatest concentration of cells, it blocks the transmittance of light to the optical sensor 254. Thus, during this step, optical sensor 254 detects little or no light from LED 256, as shown by region A on FIG. 20.

After the RBC layer has flowed past optical sensor 254, the interface between the RBC layer and the WBC/stem and progenitor cell layer begins to flow by optical sensor 254. Because this layer has a lower concentration of cells than the RBC layer, more light is detected by optical sensor 254 from LED 256. As soon as microcontroller 290 is informed by the optical sensor 254, that a pre-set amount of light transmittance has been reached, which indicates the beginning of the passage of the WBC/stem and progenitor cell composition layer, the microcontroller directs servo motor 248 to cause valve actuator cuff 246 to cause metering valve 138 to close such that the fluid flow through metering valve 138 ceases. This is shown by point D on FIG. 20. Thus, metering valve 138 closes as soon as the lowest portion of the WBC/stem and progenitor cell layer begins to reach optical sensor 254.

After this separation step, about 2 mL of packed RBC volume remains in processing bag 102, the majority of the RBC volume having been transferred into RBC concentrate bag 104. For example, in an original volume of 100 mL of collected bone marrow having a hematocrit of 30%, about 28 mL of the RBC volume (about 93%) will now be in RBC concentrate bag 104 and about 2 mL (7%) of the RBC volume will remain in processing bag 102.

5. The bag set may optionally be centrifuged in the processing device at a sufficient g force and elapsed time to restratify the cells in the processing bag into layers based on cell density and size.

This is an optional step. If this step is not performed, the method proceeds to the next step.

As a result of the previous separation step and the Coriolis forces that develop as the cell solution is removed through metering valve 138, the cell layers in the processing bag 102, which include the remaining portion of the RBC layer, all of the WBC/stem and progenitor cell layer, and all of the plasma layer, may have become somewhat less defined and more intermingled at their interfaces. In this optional step, bag set 100 in processing device 200 may be centrifuged at a pre-set g force and time sufficient to restratify the remaining cells into more defined layers by cell density and size. For example, centrifugation may be performed at about 1400×g for about 5 to about 15 minutes. This centrifugation step may be continuous with the centrifugation of the previous separation step, by programming the centrifuge to automatically increase the g force, or it may be initiated and performed after the previous centrifugation step has completed and come to a stop.

During this centrifugation step, metering valve 138 is in its closed position such that no fluid flow is permitted through metering valve 138. Centrifugation is preferably continued until the cells have been restratified into three layers with reduced intermingling at the interface between layers: a lower layer of remaining RBCs, a middle layer of WBC/stem and progenitor cells, and an upper layer of plasma. The force and time of centrifugation is sufficient such that more than 70% of the stem cells are located in the WBC/stem and progenitor cell layer, although it is preferable for at least about 80% to 90% of the stem cells to be located in this layer.

6. The bag set is centrifuged in the processing device while the metering valve rapidly opens and closes multiple times in succession to more precisely transfer a significant portion of the remaining RBCs from the processing bag into the RBC concentrate bag without also transferring the WBC/stem and progenitor cell layer.

After the previous optional restratification step, or, if the restratification step is not performed, after the previous separation step, bag set 100 in processing device 200 is centrifuged at a pre-set g force and for a pre-set period of time sufficient to complete this step and steps 7 and 8. For example, centrifugation may be performed at about 80×g, the same g force as is used in step 4, for about 5 to about 15 minutes.

In this step, a significant portion of the remaining RBCs within processing bag 102 are precisely transferred into RBC concentrate bag 104. The purpose of the lower g force is to allow the RBCs to flow from processing bag 102 into RBC concentrate bag 104 in a controlled manner with minimal risk of cell damage. This centrifugation step may be continuous with the centrifugation of the previous step, by programming the centrifuge to automatically reduce the g force if the previous step was restratification, or by continuing centrifugation at the same g force if the previous step was separation, or it may be initiated and performed after the previous centrifugation step was completed and came to a stop.

Accelerometer 291 measures the g force during centrifugation. As soon as microcontroller 290 receives input from accelerometer 291 that the pre-set g force is stable, for example, for about 30 seconds, microcontroller 290 directs servo motor 248 to cause valve actuator cuff 246 to cause metering valve 138 to open to the position which creates a fluid path from processing bag 102 through supply line 142 and into RBC concentrate bag 104, and then to close, successively repeating the opening and closing multiple times for a pre-set number of cycles for a pre-set duration at a pre-set time interval, allowing access from processing bag 102 to RBC concentrate bag 104 for repeated, discrete amounts of time sufficient to allow the plasma layer to approach the level of optical sensor 254. For example, metering valve 138 may be set to open for a duration of about 0.1 to about 0.2 sec and close for about 10 sec, repeating this cycle about 10 to about 30 times, although other combinations of the duration, interval, and repetition will also work well. As metering valve 138 opens and closes, a portion of the remaining RBCs in processing bag 102 flows into RBC concentrate bag 104. This precision red cell removal step causes approximately 1 to 1.5 mL of the 2 mL of RBC volume left remaining in processing bag 102 after the previous step to flow from processing bag 102 into RBC concentrate bag 104, reducing even further the RBC volume left in processing bag 102 and, due to the tiny volumes of RBC transferring with each brief opening and closing of metering valve 138, the RBCs do not intermingle with the stem and progenitor cells and the stem and progenitor cells do not get sucked down into the transferred red cells due to Coriolis forces. Even greater proportions of the remaining RBCs may be transferred to RBC concentrate bag 102 by this means should that be required.

This final fine metering activity is directed by microcontroller 290 which receives readings from optical sensor 254 of the transmittance of light from LED 256 as the cell layers in processing bag 102 flow by LED 256. Microcontroller 290 continues to record and analyze light transmittance as a function of time, and compares the current values to the previous values. During this step, the WBC/stem and progenitor cell layer is flowing past optical sensor 254. Because this layer has a higher cell concentration at its interface with the RBC layer and a lower cell concentration at its interface with the plasma layer, light transmittance steadily increases as the WBC/stem and progenitor cell layer flows past optical sensor 254 and the interface with the plasma layer approaches. Thus, during this step, optical sensor 254 detects a steady increase in the transmittance of light from LED 256. This is shown by the slope of the line in region B on FIG. 20.

After the WBC/stem and progenitor cell layer has flowed past optical sensor 254, the interface between the WBC/stem and progenitor cell layer and the plasma layer begins to flow by optical sensor 254. Because the plasma layer has fewer cells than the WBC/stem and progenitor cell layer, more light is detected by optical sensor 254 from LED 256. As soon as microcontroller 290 receives input from optical sensor 254 that a predetermined decrease in the rate of change of light transmittance has occurred, based on optical sensor 254 detecting a pre-set rate value, microcontroller 290 directs servo motor 248 to cause valve actuator cuff 246 to cause metering valve 138 to close such that the transfer of RBCs through metering valve 138 ends. This is shown by point E on FIG. 20, at the transition from the steep slope of the line in region B to the almost horizontal line in region C, which is the point at which the WBC/stem and progenitor cell composition layer has passed below optical sensor 254 and the plasma layer has begun to flow past optical sensor 254. Thus, metering valve 138 closes as soon as the lowest portion of the plasma layer begins to reach optical sensor 254.

After this separation step, about 0.5 to 1.0 mL of RBC volume remains in processing bag 102, another 1 to 1.5 mL of RBC volume having been transferred into RBC concentrate bag 104.

7. While the bag set is being centrifuged, the processing device tares the weight of the empty stem cell bag to zero.

After metering valve 138 has closed in the previous step, centrifugation continues at the g force and for the time set in step 6. Accelerometer 291 confirms the set g force, at which point load cell 272 and microcontroller 290 combine to tare the weight of the empty stem cell bag 106 to zero.

8. The bag set is centrifuged in the processing device while the metering valve rapidly opens and closes multiple times in succession to separate and transfer the small amount of remaining RBCs, the WBC/stem and progenitor cell layer, and some plasma from the processing bag into the stem cell bag.

Centrifugation of bag set 106 in processing device 200 continues at the g force and for the time set in step 6. When microcontroller 290 receives input from load cell 272 that the weight of the empty stem cell bag 106 has been tared to zero, microcontroller 290 directs servo motor 248 to cause valve actuator cuff 246 to cause metering valve 138 to open to the position which creates a fluid path from processing bag 102 through supply line 156 and stem cell bag inlet line 152 into stem cell bag 106, and then to close, successively repeating the opening and closing multiple times for a pre-set number of cycles for a pre-set duration at a pre-set time interval, allowing access from processing bag 102 to stem cell bag 106 for repeated, discrete amounts of time sufficient to allow stem cell bag 106 to be filled until its pre-set weight is reached. For example, metering valve 138 may be set to open for duration of about 0.1 to about 0.2 sec and close for about 10 sec, repeating this cycle multiple times. As metering valve 138 opens and closes, the remaining RBCs, the WBC/stem and progenitor cell layer, and some plasma in processing bag 102 flow into stem cell bag 106. The purpose of the lower g force during this step is to allow these cells to flow from processing bag 102 into stem cell bag 106 in a controlled manner with minimal risk of the cell damage that would occur at higher g forces.

During this separation step, load cell 272 measures the weight of stem cell bag 106 and microcontroller 290 receives that input from load cell 272. The desired weight of the WBC/stem and progenitor cell layer is pre-set, and may be set from about 3 grams to about 30 grams. For example, a weight of ten grams may be used if the desired volume of the final stem cell product in stem cell bags 106 is 10 mL. As soon as microcontroller 290 receives input from load cell 272 that stem cell bag 106 has reached its pre-set weight, microcontroller 290 directs servo motor 248 to cause valve actuator cuff 246 to cause metering valve 138 to close such that fluid flow through metering valve 138 stops.

After metering valve 138 closes, centrifugation continues at the same g force until the pre-set time period set in step 6 has been reached.

9. Centrifugation ends and the bag set is removed from the processing device.

At the end of the pre-set centrifugation period, the centrifugation stops and processing device 200 is removed from the centrifuge. Bag set 100, including all of the bags, metering valve 138, and lines are taken out of processing unit 200.

Stem cell bag 106 contains the remaining RBCs, the WBC/stem and progenitor cells, and some plasma. The contents of stem cell bag 106 are referred to herein as the "stem cell composition" or the "composition of stem cells." RBC concentrate bag 104 contains RBCs. Processing bag 102 contains the remainder of the plasma not contained in stem cell bag 106.

If desired, samples from RBC concentrate bag 104 and stem cell bag 106 may be taken. Sampling line 162, sampling pillow 168, sampling site 166, and line clamp 164 are used to sample stem cell bag 106.

If the stem cell composition is to be used immediately, for instance in the autologous setting, stem cell bag 106 is then separated from the rest of bag set 100 using a Sebra sealer (Sebra Corp., Tucson, Ariz.)

If the stem cell composition is to be frozen, a cryoprotectant solution, such as a DMSO solution, should be added to stem cell bag 106 through sterile filter 174 and cryoprotectant supply line 165.

EXAMPLES OF METHOD USING BONE MARROW AND CORD BLOOD AS SOURCES OF STEM CELLS

Five units of human bone marrow and six units of cord blood were collected from authorized vendors and processed within 1-3 days of collection. The tables below show the data obtained for the bone marrow and cord blood processed by the method described herein. The bone marrow was anticoagulated with heparin and the cord blood with CPD. A tabletop centrifuge sized to contain the processing device provided the centrifugal fields. No xenobiotic additives were used in these experiments as sedimentation aids. Table 1 below provides a summary of the method steps utilized for the bone marrow and cord blood experiments.

TABLE 1

Summary of Method for Bone Marrow and Cord Blood Experiments

| Step | Method Description | Bone Marrow Experiments 1, 2 and 3 and all cord blood experiments | Bone Marrow Experiments 4 and 5 |
|---|---|---|---|
| 1 | The bone marrow or cord blood is transferred into the processing bag. | yes | yes |
| 2 | The loaded bag set is placed into the processing device. | yes | yes |
| 3 | The bag set is centrifuged in the processing device at a sufficient g force and time to stratify the cells of the bone marrow or cord blood in the processing bag into layers based on their density and size. | yes, centrifugation at 1400 × g for 40 minutes | yes, centrifugation at 1400 × g for 40 minutes |
| 4 | The bag set is centrifuged in the processing device at a lower g force to allow separation and transfer of most of the RBCs from the processing bag into the RBC concentrate bag. | yes, centrifugation at 80 × g for 5 minutes | yes, centrifugation at 80 × g for 15 minutes |
| 5 | The bag set may optionally be centrifuged in the processing device at a sufficient g force and time to restratify the cells in the processing bag into layers based on cell density and size. | yes, centrifugation at 1400 × g for 10 minutes | no, optional step omitted |
| 6 | The bag set is centrifuged in the processing device while the metering valve rapidly opens and closes multiple times in succession to separate a portion of the remaining RBCs from the processing bag into the RBC concentrate bag without also transferring the WBC/stem and progenitor cell layer. | yes, centrifugation at 80 × g for 10 minutes | yes, centrifugation continues at 80 × g from step 4 |
| 7 | While the bag set is being centrifuged, the processing device tares the weight of the empty stem cell bag to zero. | yes | yes |
| 8 | The bag set is centrifuged in the processing device while the metering valve rapidly opens and closes multiple times in succession to separate and transfer the small amount of remaining RBCs, the WBC/stem and progenitor cell layer, and some plasma from the processing bag into the stem cell bag. | yes, centrifugation of 80 × g of step 6 | yes, centrifugation continues at 80 × g from step 4 |

Samples of bone marrow and cord blood were taken before processing and samples of the final product (stem cell composition) were taken after processing. Cell counts of RBCs, WBCs, platelets, neutrophils, lymphocytes, and monocytes were performed using a Sysmex XE-2100. Enumeration of CD34+ cells and CD45+ cells (an antigen expressed on all leukocytes and on most CD34+ cells) were performed on samples before and after processing using a commercial Stem-Count kit (Beckman Coulter, Inc, Miami, Fla.) according to the manufacturer's instructions. The kit allows the simultaneous identification and enumeration of CD45+ and dual-positive CD45+, CD34+ cell population percentages and absolute cell counts in biological specimens by flow cytometry. Viability of CD45+ cells was determined on the basis of dye exclusion of the vital stain 7-AAD. Cell population measurements were obtained by flow cytometry with appropriate gating and analysis on an appropriately configured Beckman Coulter FC-500 flow cytometer (Beckman Coulter, Inc., Miami, Fla.). Identification and enumeration of ALDH Br+ cells were performed before and after processing on samples from bone marrow units 1, 2 and 3 using the commercially available Aldecount kit (Aldagen, Durham, N.C.) with the Beckman Coulter FC-500 flow cytometer according to the manufacturer's instructions. The reagent provided in the kit causes stem cells to be stained a bright fluorescent green. These cells are designated as Aldagen bright (ALDH Br+) cells.

A. Bone Marrow Data

Table 2 shows the volume and cell counts of the bone marrow for the five experiments prior to processing. The total number of RBCs, platelets, TNCs, neutrophils, lymphocytes, monocytes, MNCs, CD34+ cells, and ALDH Br+ cells in each unit are shown. The entry of ND indicates the data was "not determined".

TABLE 2

Bone Marrow Preprocessing (Volume and Total Cell Counts per Bone Marrow Unit)

| Exp. | Unit Volume (mL) | RBC $10^6$/unit | Platelet $10^6$/unit | TNC $10^6$/unit | Neutrophil $10^6$/unit | Lymphocyte $10^6$/unit | Monocyte $10^6$/unit | MNC $10^6$/unit | CD34+ Cell $10^6$/unit | ALDH Br+ $10^6$/unit |
|---|---|---|---|---|---|---|---|---|---|---|
| 1 | 83 | 329,000 | 5,390 | 1636 | 843 | 412 | 124 | 536 | 8.18 | 13.09 |
| 2 | 154 | 427,000 | 6,140 | 2229 | 1157 | 429 | 183 | 611 | 19.50 | 17.61 |
| 3 | 149 | 467,000 | 5,970 | 1904 | 1060 | 346 | 119 | 466 | 17.23 | 23.41 |
| 4 | 78 | 189,000 | 5,280 | 1723 | 1180 | 109 | 132 | 241 | 8.96 | ND |
| 5 | 78 | 170,000 | 6,720 | 1728 | 1235 | 133 | 149 | 281 | 9.50 | ND |
| mean | 108 | 317,000 | 5,900 | 1844 | 1095 | 286 | 141 | 427 | 12.7 | 18.04 |
| SD | 39 | 135,000 | 590 | 236 | 155 | 154 | 26 | 161 | 5.3 | 5.18 |

Table 3 shows the volume and cell counts for the stem cell compositions obtained in the five experiments from the five units of bone marrow referred to in Table 2. The total number of RBCs, platelets, TNCs, neutrophils, lymphocytes, monocytes, MNCs, CD34+ cells, and ALDH Br+ cells in each unit are shown.

TABLE 3

Bone Marrow Stem Cell Composition (Volume and Total Cell Counts per Bone Marrow Unit)

| Exp. | Unit Volume (mL) | RBC $10^6$/unit | Platelet $10^6$/unit | TNC $10^6$/unit | Neutrophil $10^6$/unit | Lymphocyte $10^6$/unit | Monocyte $10^6$/unit | MNC $10^6$/unit | CD34+ Cell $10^6$/unit | ALDH Br+ $10^6$/unit |
|---|---|---|---|---|---|---|---|---|---|---|
| 1 | 20.9 | 6,700 | 5,710 | 1271 | 531 | 374 | 98.2 | 472 | 8.6 | 11.4 |
| 2 | 20.7 | 6,210 | 6,090 | 1482 | 600 | 339 | 161.5 | 501 | 19.7 | 20.2 |
| 3 | 21.3 | 6,390 | 6,010 | 1325 | 552 | 264 | 98 | 362 | 13.7 | 17.4 |
| 4 | 21 | 6,090 | 4,530 | 1407 | 880 | 170 | 79.8 | 250 | 9.7 | ND |
| 5 | 20.8 | 4,160 | 6,010 | 1075 | 647 | 96 | 106.1 | 202 | 9.5 | ND |
| mean | 20.9 | 5910.0 | 5670.0 | 1312.0 | 642.0 | 248.6 | 108.7 | 357.4 | 12.2 | 16.3 |
| SD | 0.2 | 1004.9 | 653.6 | 154.9 | 140.4 | 115.8 | 31.0 | 131.8 | 4.6 | 4.5 |

Table 4 presents the percent recovery of each cell type based on the results of the five experiments presented in Tables 2 and 3. The percent recovery was calculated by dividing the cell count in the stem cell composition (Table 3) by the corresponding value in the bone marrow preprocessing samples (Table 2) and multiplying this quotient by 100. For example, in Experiment 1, the percent recovery of RBCs was calculated by dividing $(6,700\times10^6)$ by $(329,000\times10^6)$ and multiplying the quotient by 100, to give a recovery of 2.0% (Table 4). The percent depletion can be simply calculated by subtracting the percent recovery from 100%. For example, in Experiment 1, the percent depletion of red cells was 100%-2.0%=98.0%.

stem cells as measured by CD34+ cells and ALDH Br+ cells (average recoveries of 98.9% and 92.0%, respectively). Even more unexpectedly, Table 4 demonstrates that more than 90% of the stem cells can be recovered even while recovering on average only 59% of the neutrophils. This level of selective cell separation of bone marrow would be expected to require the use of a xenobiotic sedimentation agent.

Tables 5 and 6 show the ratios of RBCs to the nucleated cell types in the preprocessing bone marrow and in the stem cell compositions, based on the data of Tables 2 and 3. The ratios of these cells to each other define unique stem cell compositions not found in nature nor produced by any other cell processing system. The development of a stem cell composition with the very low number of RBCs represents an important advancement for stem cell therapy by having created a safer cell product due to the adverse effects associated with excess red cells for stem cell transfusions and a cell product conducive to further purification processes with immunoaf-

TABLE 4

Percent Cell Recovery of Each Cell Type in the Bone Marrow Stem Cell Composition

| Exp. | RBC | Platelet | TNC | Neutrophil | Lymphocyte | Monocyte | MNC | CD34+ Cell | ALDH Br+ |
|---|---|---|---|---|---|---|---|---|---|
| 1 | 2.0 | 105.9 | 77.7 | 63.0 | 90.8 | 79.2 | 88.1 | 105.1 | 87.1 |
| 2 | 1.5 | 99.2 | 66.5 | 51.9 | 79.0 | 88.3 | 82.0 | 101.0 | 114.7 |
| 3 | 1.4 | 100.7 | 69.6 | 52.1 | 76.3 | 82.4 | 77.7 | 79.5 | 74.3 |
| 4 | 3.2 | 85.8 | 81.7 | 74.6 | 156.0 | 60.5 | 103.7 | 108.3 | ND |
| 5 | 2.4 | 89.4 | 62.2 | 52.4 | 72.2 | 71.2 | 71.9 | 100.0 | ND |
| mean | 2.1 | 96.2 | 71.5 | 58.8 | 94.8 | 76.3 | 84.7 | 98.8 | 92.0 |
| SD | 0.8 | 8.3 | 8.0 | 10.0 | 34.9 | 10.8 | 12.2 | 11.3 | 20.6 |

The data in Table 4 unexpectedly demonstrate that it was possible to achieve on average a 97.9% depletion of RBCs (2.1% recovery) while recovering greater than 90% of the finity or flow cytometric methods. Specifically, the data in Tables 5 and 6 show that in the preprocessing bone marrow, the mean ratio of RBCs to CD34+ cells was initially 25,642:1 and after processing, the ratio in the stem cell composition was 539:1. This dramatic reduction in the RBC to stem cell ratio reflects the success of the method to selectively eliminate RBCs without loss of CD34+ cells. Similar reductions in the ratio of red cells to ALDH Br+ cells were observed.

The utility of these cell populations is inherent to their containing viable cells. Table 7 contains the analysis results for cell viability of the CD45+ cells in the bone marrow as measured using a commercial kit (Stem-Kit, Beckman Coulter, Fullerton, Calif.). There was no significant change in the viability of the CD45+ cells post-processing which demonstrates the biocompatibility of the process.

TABLE 5

Ratio of RBCs to Nucleated Cells in the Bone Marrow Unit (Preprocessing)

| Exp. | RBC: TNC | RBC: Neutrophil | RBC: Lymph | RBC: Monocytes | RBC: MNC | RBC: CD34+ | RBC: ALDH Br+ |
|---|---|---|---|---|---|---|---|
| 1 | 201 | 390 | 799 | 2653 | 614 | 40220 | 25134 |
| 2 | 192 | 369 | 995 | 2333 | 699 | 21897 | 24248 |
| 3 | 245 | 441 | 1350 | 3924 | 1002 | 27104 | 19949 |
| 4 | 110 | 160 | 1734 | 1432 | 784 | 21094 | ND |
| 5 | 98 | 138 | 1278 | 1141 | 605 | 17895 | ND |
| mean | 169 | 300 | 1231 | 2297 | 741 | 25642 | 23110 |
| SD | 63 | 140 | 358 | 1102 | 163 | 8795 | 2773 |

TABLE 6

Ratio of RBCs to Nucleated Cells in the Bone Marrow Stem Cell Composition

| Exp. | RBC: TNC | RBC: Neutrophil | RBC: Lymph | RBC: Monocytes | RBC: MNC | RBC: CD34+ | RBC: ALDH Br+ |
|---|---|---|---|---|---|---|---|
| 1 | 6 | 14 | 20 | 75 | 16 | 847 | 640 |
| 2 | 4 | 10 | 18 | 38 | 12 | 315 | 308 |
| 3 | 5 | 12 | 24 | 65 | 18 | 468 | 368 |
| 4 | 4 | 7 | 36 | 76 | 24 | 627 | ND |
| 5 | 4 | 6 | 43 | 39 | 21 | 437 | ND |
| mean | 5 | 10 | 28 | 59 | 18 | 539 | 439 |
| SD | 1 | 3 | 11 | 19 | 5 | 205 | 177 |

TABLE 7

Percent of Viable CD45+ Cells in the Bone Marrow Preprocessing and in the Stem Cell Composition

| Exp. | % Viable CD45+ Cells in Bone Marrow Preprocessing | % Viable CD45+ Cells in Stem Cell Composition |
|---|---|---|
| 1 | 76.0 | 79.8 |
| 2 | 83.0 | 82.0 |
| 3 | 82.0 | 84.0 |
| 4 | 92.3 | 93.5 |
| 5 | 94.2 | 91.9 |
| mean | 85.5 | 86.2 |
| SD | 7.6 | 6.1 |

B. Cord Blood Data

Table 8 shows the volume and cell counts of six cord blood units prior to processing. The total number of RBCs, platelets, TNCs, neutrophils, lymphocytes, monocytes, MNCs, and CD34+ cells in each unit before processing are shown.

TABLE 8

Cord Blood Preprocessing (Volume and Total Cell Counts per Cord Blood Unit)

| Exp. | Unit Volume (mL) | RBC $10^6$/unit | Plt.* $10^6$/unit | TNC $10^6$/unit | Neut. $10^6$/unit | Lymph. $10^6$/unit | Mono. $10^6$/unit | MNC $10^6$/unit | CD34+ cell $10^6$/unit |
|---|---|---|---|---|---|---|---|---|---|
| 1 | 114 | 370170 | 25478 | 880 | 483 | 239 | 103 | 342 | 11.7 |
| 2 | 90 | 332394 | 16258 | 789 | 535 | 146 | 60 | 206 | 6.47 |
| 3 | 127 | 462065 | 28483 | 2852 | 1290 | 1144 | 242 | 1386 | 2.99 |
| 4 | 89 | 302792 | 22311 | 799 | 460 | 256 | 62 | 318 | 1.12 |
| 5 | 92 | 322158 | 30843 | 745 | 403 | 212 | 102 | 314 | 0.89 |
| 6 | 80 | 272902 | 15720 | 575 | 295 | 251 | 18 | 269 | 0.8 |
| mean | 98.7 | 343746.8 | 23182.2 | 1106.7 | 577.7 | 374.7 | 97.8 | 472.5 | 4.0 |
| SD | 17.9 | 66315.3 | 6268.1 | 861.0 | 358.5 | 379.1 | 77.4 | 450.1 | 4.4 |

*Plt. = platelets, Neut. = neutrophils, Lymph. = lymphocytes, Mono. = monocytes

Table 9 shows the volume and cell counts for the stem cell compositions obtained in the six experiments from the corresponding units of cord blood referred to in Table 8. The total number of RBCs, platelets, TNCs, neutrophils, lymphocytes, monocytes, MNCs, and CD34+ cells in each unit are shown after processing.

TABLE 9

Cord Blood Stem Cell Composition. (Volume and Total Cell Counts per Cord Blood Unit)

| Exp. | Unit Volume (mL) | RBC $10^6$/unit | Plt.* $10^6$/unit | TNC $10^6$/unit | Neut. $10^6$/unit | Lymph. $10^6$/unit | Mono. $10^6$/unit | MNC $10^6$/unit | CD34+ cell $10^6$/unit |
|---|---|---|---|---|---|---|---|---|---|
| 1 | 12 | 2070 | 5971 | 432 | 115 | 191 | 99 | 308 | 11.33 |
| 2 | 11 | 9990 | 11988 | 651 | 367 | 186 | 58 | 244 | 5.77 |
| 3 | 11 | 3996 | 21079 | 1386 | 287 | 878 | 202 | 1080 | 2.29 |
| 4 | 11 | 5016 | 19152 | 535 | 207 | 250 | 71 | 320 | 1.12 |
| 5 | 11 | 12744 | 20736 | 610 | 329 | 192 | 76 | 268 | 0.82 |
| 6 | 12 | 5980 | 15077 | 571 | 269 | 256 | 21 | 277 | 0.94 |
| mean | 11.3 | 6632.7 | 15667.2 | 697.5 | 262.3 | 325.5 | 87.8 | 416.2 | 3.7 |
| SD | 0.5 | 3985.7 | 5916.5 | 345.5 | 90.4 | 272.5 | 61.5 | 326.4 | 4.2 |

*Plt. = platelets, Neut. = neutrophils, Lymph. = lymphocytes, Mono. = monocytes

Table 10 presents the percent recovery of each cell type based on the results of the six experiments presented in Tables 8 and 9. The percent recovery was calculated by dividing the cell count in the stem cell composition (Table 9) by the corresponding value in the cord blood preprocessing samples (Table 8) and multiplying this quotient by 100.

TABLE 10

Percent Cell Recovery of Each Cord Blood Cell Type in the Stem Cell Composition

| Exp. | RBC | Plt.* | TNC | Neut. | Lymph. | Mono. | MNC | CD34+ cells |
|---|---|---|---|---|---|---|---|---|
| 1 | 0.6 | 23.4 | 49.1 | 23.8 | 79.9 | 96.1 | 90.1 | 96.8 |
| 2 | 3.0 | 73.7 | 82.5 | 68.6 | 127.4 | 96.7 | 118.4 | 89.2 |
| 3 | 0.9 | 74.0 | 48.6 | 22.2 | 76.7 | 83.5 | 77.9 | 76.6 |
| 4 | 1.7 | 85.8 | 67.0 | 45.0 | 97.7 | 114.5 | 100.6 | 100.0 |
| 5 | 4.0 | 67.2 | 81.9 | 81.6 | 90.6 | 74.5 | 85.4 | 92.1 |
| 6 | 2.2 | 95.9 | 99.3 | 91.2 | 102.0 | 116.7 | 103.0 | 117.5 |
| mean | 2.0 | 70.0 | 71.4 | 55.4 | 95.7 | 97.0 | 95.9 | 95.4 |
| SD | 1.3 | 25.0 | 20.2 | 29.5 | 18.3 | 16.6 | 14.5 | 13.5 |

*Plt. = platelets, Neut. = neutrophils, Lymph. = lymphocytes, Mono. = monocytes

The data in Table 10 demonstrate that it was possible to achieve a 98.0% on average depletion of RBCs (2.0% recovery) while recovering on average 95% of the stem cells as measured by the CD34+ marker. Further, Table 10 demonstrates that an average of 95% of the stem cells were recovered even while only recovering on average 55% of the neutrophils. As with bone marrow, it would be expected to require the use of a xenobiotic sedimentation aid to achieve this level of selective cell separation.

Tables 11 and 12 below show the ratios of RBCs to various other cell types in the preprocessing cord blood and in the cord blood stem cell compositions, based on the data of Tables 8 and 9. The ratios of these cells to each other, without the presence of xenobiotic additive, define unique stem cell compositions not found in nature nor produced by any other cell processing system. The utility of these stem cell compositions requires the stem cells be viable, with a significant depletion of red cells and no xenobiotic additives. The availability of stem cell compositions containing most of the stem and progenitor cells resident in the source bone marrow or cord blood and with very low RBC to CD34+ cell ratios represents an important advancement for stem cell therapy by having created a safer cell product due to the potential adverse effects associated with excess red cells for stem cell transfusions.

The mean ratio of RBCs to CD34+ cells was initially 201,834:1 and after processing it was reduced to 5,007:1. This dramatic reduction in RBC to stem cell ratio reflects the success of the method to selectively eliminate RBCs without significant loss of CD34+ cells.

TABLE 11

Ratio of RBCs to Nucleated Cells in the Cord Blood Unit (Preprocessing)

| Exp. | RBC: TNC | RBC: Neut.* | RBC: Lymph. | RBC: Mono. | RBC: MNC | RBC: CD34+ |
|---|---|---|---|---|---|---|
| 1 | 421 | 766 | 1549 | 3594 | 1082 | 31638 |
| 2 | 421 | 621 | 2277 | 5540 | 1614 | 51375 |
| 3 | 162 | 358 | 404 | 1909 | 333 | 154537 |
| 4 | 379 | 658 | 1183 | 4884 | 952 | 270350 |
| 5 | 432 | 799 | 1520 | 3158 | 1026 | 361975 |
| 6 | 475 | 925 | 1087 | 15161 | 1015 | 341128 |
| mean | 382 | 688 | 1337 | 5708 | 1004 | 201834 |
| SD | 112 | 194 | 619 | 4806 | 408 | 143933 |

*Neut. = neutrophils, Lymph. = lymphocytes, Mono. = monocytes

TABLE 12

Ratio of RBCs to Nucleated Cells in the Cord
Blood Stem Cell Composition

| Exp. | RBC:TNC | RBC:Neut. | RBC:Lymph. | RBC:Mono. | RBC:MNC | RBC:CD34+ |
|---|---|---|---|---|---|---|
| 1 | 5 | 18 | 11 | 21 | 7 | 183 |
| 2 | 15 | 27 | 54 | 172 | 41 | 1731 |
| 3 | 3 | 14 | 5 | 20 | 4 | 1745 |
| 4 | 9 | 24 | 20 | 71 | 16 | 4479 |
| 5 | 21 | 39 | 66 | 168 | 48 | 15541 |
| 6 | 10 | 22 | 23 | 285 | 22 | 6362 |
| mean | 11 | 24 | 30 | 123 | 23 | 5007 |
| SD | 7 | 9 | 25 | 104 | 18 | 5617 |

*Neut. = neutrophils, Lymph. = lymphocytes, Mono. = monocytes

The utility of these cell populations is inherent to their containing viable cells. Table 13 contains the analysis results for cell viability of the CD45+ cells in the cord blood as measured using the Stem-Kit. There was no significant change in the viability of the CD45+ cells which is an accepted surrogate to demonstrate the maintenance of stem cell viability in cord blood products post-processing.

TABLE 13

Percent of Viable CD45+ Cells in the Cord Blood Pre-
processing and in the Cord Blood Stem Cell Composition

| Exp. | % Viable CD45+ Cells in Cord Blood Preprocessing | % Viable CD45+ Cells in Cord Blood Stem Cell Composition |
|---|---|---|
| 1 | 82 | 75 |
| 2 | 61 | 61 |
| 3 | 96 | 94 |
| 4 | 79 | 77 |
| 5 | 88 | 88 |
| 6 | 74 | 72 |
| mean | 80.0 | 77.8 |
| SD | 11.9 | 11.9 |

Stem Cell Compositions

The method as described above yields compositions of stem cells derived from bone marrow or cord blood that include stem cells, plasma, RBCs, and WBCs, and that have no xenobiotic additives. The stem cell composition derived from bone marrow has a ratio of about 5 RBCs for each TNC, about 10 RBCs for each neutrophil, about 18 RBCs for each MNC, and about 400-500 RBCs for each stem cell as measured by CD34+ cells or ALDH Br+ cells (Table 6). The stem cell composition derived from cord blood has a ratio of about 11 RBCs for each TNC, about 24 RBCs for each neutrophil, about 23 RBCs for each MNC, and about 5,000 RBCs for each stem cell as measured by CD34+ cells (Table 12).

The stem cell composition derived from bone marrow recovered about 79% to about 100% of CD34+ cells, and about 74% to about 100% of ALDH Br+ cells, while depleting about 97% to about 99% of RBCs. The stem cell composition derived from cord blood recovered greater than about 77% to about 100% of CD34+ cells, while depleting about 96% to about 99% of RBCs.

The results demonstrate the unexpected finding that the stem cells in bone marrow or cord blood can maintain their relatively higher position in the WBC/stem and progenitor cell layer (closer to the plasma layer than the red cell layer) and that the neutrophils maintain their relatively lower position in the WBC/stem and progenitor cell layer (closer to the red cell layer) throughout the process of separating and transferring RBCs from the processing bag into the RBC concentrate bag. It would be expected that the RBCs flowing out of the processing bag would cause significant mixing of the stem cells, neutrophils and red cells as well as other cell types due to Coriolis effects and non-laminar flow as the RBCs flow downward toward the metering valve. Such mixing would have been expected to preclude the observed high recovery of stem cells relative to the low recovery of neutrophils, and the high recovery of stem cells relative to the highly efficient depletion of RBCs.

The invention has been described above with reference to certain embodiments. Those skilled in the art may envision other embodiments and variations of the invention that fall within the scope of the claims.

We claim:

1. A system for preparing a stem cell product from bone marrow or cord blood, comprising:
   a. a bag set, including a processing bag to hold collected bone marrow or cord blood, a red blood cell concentrate bag, a stem cell bag, and a metering valve, wherein said metering valve is connected to said processing bag, said red blood cell concentrate bag, and said stem cell bag;
   b. a processing device, within which said bag set fits, and including a microcontroller, a motor, an optical sensor, an LED, a load cell, and an accelerometer;
   c. said microcontroller operatively coupled to said motor, said optical sensor, said LED, said load cell, and said accelerometer;
   d. said motor operatively coupled to said metering valve when said bag set is contained in said processing device;
   e. wherein said microcontroller is configured to receive input from said accelerometer that said bag set is being centrifuged, in said processing device, with said metering valve closed, at a first g force that is sufficient to stratify the bone marrow or cord blood in said processing bag into a layer comprising red blood cells, a layer comprising white blood/stem cells and progenitor cells, and a layer comprising plasma; and
   f. wherein said microcontroller is configured to receive, after the bone marrow or cord blood is stratified in said processing bag, input from said accelerometer that said bag set is being centrifuged in said processing device at a second g force that is lower than said first g force, and then to direct said motor to cause said metering valve to open a fluid path between said processing bag and said red blood cell concentrate bag to allow transfer of a substantial portion of said red blood cells from said processing bag to said red blood cell concentrate bag, and then to direct said motor to cause said metering valve to close said fluid path between said processing bag and said red blood cell concentrate bag in response to said optical sensor detecting set amount of light transmittance from said LED through said processing bag at a level between a top edge and a bottom outlet of said processing bag; and
   g. wherein said microcontroller is configured to receive, after causing said metering valve to close said fluid path between said processing bag and said red blood cell concentrate bag, input from said accelerometer that said bag set is being centrifuged in said processing device at a third g force, and then to direct said motor to cause said metering valve to open and close said fluid path between said processing bag and said red blood cell concentrate bag multiple times in succession to successively repeat opening and closing said fluid path between said processing bag and said red blood cell concentrate bag for repeated, discrete amounts of time in succession to allow transfer of a further portion of said red blood cells from said processing bag to said red blood cell concentrate bag, and then to direct said motor to cause said metering valve to close said fluid path between said processing bag and said red blood cell concentrate bag in response to said optical sensor detecting a decrease in a rate of change of light transmittance from said LED through said processing bag at said level between said top edge and said bottom outlet of said processing bag; and h. wherein said microcontroller is configured to tare said stem cell bag to zero in response to an input received by said microcontroller from said load cell measuring a weight of said stem cell bag; and i. wherein said microcontroller is configured to direct, after said stem cell bag is tared to zero, said motor to cause said metering valve to open and close a fluid path between said processing bag and said stem cell bag multiple times in succession to successively repeat opening and closing said fluid path between said processing bag and said stem cell bag for repeated, discrete amounts of time in succession sufficient to transfer at least remaining red blood cells and the layer of white blood/stem cells and progenitor cells into said stem cell bag, and then to direct said motor to cause said metering valve to close said fluid path between said processing bag and said stem cell bag in response to receipt by said microcontroller of an input from said load cell of a pre-set weight.

2. The system of claim 1, wherein said optical sensor is located in said processing device such that the volume in said processing bag between the level of said optical sensor and the level of said metering valve is about 2 mL.

3. The system of claim 1 wherein said microcontroller is configured to receive, after step (f) and before step (g), input from said accelerometer that said bag set is being centrifuged in said processing device, with said metering valve closed, at a fourth g force that is sufficient to restratify the bone marrow or cord blood in said processing bag into a layer comprising red blood cells, a layer comprising white blood/stem cells and progenitor cells, and a layer comprising plasma.

4. The system of claim 1 wherein said second and said third g forces are lower than said first g force and wherein said fourth g force is equal to said first g force.

5. A system for preparing a stein cell product from bone marrow or cord blood, comprising:

a bag set, including a processing bag to hold collected bone marrow or cord blood, a red blood cell concentrate bag, a stem cell bag, and a metering valve, wherein said metering valve is connected to said processing bag, said red blood cell concentrate bag, and said stem cell bag;

a processing device, within which said bag set fits;

a load cell means for measuring a weight of said stem cell bag;

an accelerometer means for measuring a g force of centrifugation of said processing device containing said bag set;

an optical sensor means for measuring light transmittance from an LED through said processing bag;

means for receiving a first, accelerometer means measured, g force of centrifugation of said processing device containing said bag set, with said metering valve closed, for a period of time sufficient to stratify the bone marrow or cord blood in said processing bag into a layer comprising red blood cells, a layer comprising white blood/stem cells and progenitor cells, and a layer comprising plasma;

means for opening said metering valve at a second, accelerometer means measured, g force of centrifugation of said processing device containing said bag set for opening a fluid path between said processing bag containing said stratified bone marrow or cord blood and said red blood cell concentrate bag to allow transfer of a substantial portion of said red blood cells from said processing bag to said red blood cell concentrate bag and for closing said metering valve as a function of a set amount of optical sensor means measured transmittance of light from said LED through said processing bag for closing said fluid path; and means for opening and closing said metering valve multiple times in succession at a third, accelerometer means measured, g force of centrifugation of said processing device containing said bag set to successively repeat opening and closing said fluid path between said processing bag and said red blood cell concentrate bag for repeated, discrete amounts of time in succession sufficient to allow transfer of a further portion of said red blood cells from said processing bag to said red blood cell concentrate bag and for closing said metering valve as a function of said optical sensor means detecting a decrease in a rate of change of light transmittance from said LED through said processing bag; and means for opening and closing said metering valve multiple times in succession to successively repeat opening and closing a fluid path between said processing bag and said stem cell bag for repeated, discrete amounts of time in succession sufficient to transfer at least remaining red blood cells and the layer of white blood/stem cells and progenitor cells into said stem cell bag and for closing said metering valve as a function of a pre-set, load cell means measured, weight of said stem cell bag.

\* \* \* \* \*